US010993823B2

(12) United States Patent
Hopkins et al.

(10) Patent No.: US 10,993,823 B2
(45) Date of Patent: May 4, 2021

(54) SYSTEMS AND METHODS FOR DEPLOYING A PORTION OF A STENT USING AT LEAST ONE COILED MEMBER

(71) Applicant: COOK MEDICAL TECHNOLOGIES LLC, Bloomington, IN (US)

(72) Inventors: Tony C. Hopkins, Bloomington, IN (US); Siddharth Vad, Irvine, CA (US); Michael P. DeBruyne, Bloomington, IN (US); Zachary Wagner, Noblesville, IN (US); Blayne A. Roeder, Bloomington, IN (US); William J. Havel, West Lafayette, IN (US); Jarin Kratzberg, West Lafayette, IN (US); Rick Hadley, Otterbein, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 235 days.

(21) Appl. No.: 16/057,149

(22) Filed: Aug. 7, 2018

(65) Prior Publication Data
US 2018/0338848 A1 Nov. 29, 2018

Related U.S. Application Data

(60) Continuation of application No. 14/867,791, filed on Sep. 28, 2015, now Pat. No. 10,064,746, which is a (Continued)

(51) Int. Cl.
A61F 2/95 (2013.01)
A61F 2/92 (2013.01)
(52) U.S. Cl.
CPC ............... A61F 2/95 (2013.01); A61F 2/92 (2013.01); A61F 2002/9511 (2013.01)

(58) Field of Classification Search
CPC ............... A61F 2002/9511; A61F 2/95; A61F 2002/9505; A61F 2002/9665; A61F 2002/9522; A61F 2002/011; A61F 2/82
See application file for complete search history.

(56) References Cited

U.S. PATENT DOCUMENTS 5,201,757 A 4/1993 Heyn et al.
5,480,423 A 1/1996 Ravenscroft et al.
(Continued)

FOREIGN PATENT DOCUMENTS

CN 102014805 4/2011
DE 102006053748 4/2008
(Continued)

OTHER PUBLICATIONS

European Search Report for Application No. 13171753 dated Oct. 21, 2013, 7 pgs.
(Continued)

Primary Examiner — Katherine M Shi
(74) Attorney, Agent, or Firm — Brinks Gilson & Lione

(57) ABSTRACT

The present embodiments provide systems and methods for deploying at least a portion of a stent. In one embodiment, the system comprises a cannula having an outer surface, and at least one coiled member having proximal and distal ends and a plurality of turns disposed therebetween. One of the proximal and distal ends of the coiled member is secured to the outer surface of the cannula, and the other of the proximal and distal ends of the coiled member is unsecured relative to the outer surface of the cannula. A portion of a stent is looped around the unsecured end of the coiled member and disposed within spacing between adjacent turns of the coiled member. Rotation of the cannula subsequently causes the portion of the stent to disengage from the coiled member.

19 Claims, 16 Drawing Sheets

Related U.S. Application Data division of application No. 13/796,395, filed on Mar. 12, 2013, now Pat. No. 9,173,756.

(60) Provisional application No. 61/659,255, filed on Jun. 13, 2012, provisional application No. 61/745,181, filed on Dec. 21, 2012.

(56) References Cited

U.S. PATENT DOCUMENTS

| | | | |
|---|---|---|---|
| 5,824,041 | A | 10/1998 | Lenker et al. |
| 5,824,058 | A | 10/1998 | Ravenscroft |
| 6,068,634 | A | 5/2000 | Lorentzen Cornelius et al. |
| 6,077,296 | A | 6/2000 | Shokoohi et al. |
| 6,872,224 | B1 | 3/2005 | Telxelra Moretra et al. |
| 7,101,390 | B2 | 9/2006 | Nelson |
| 7,147,657 | B2 | 12/2006 | Chiang |
| 7,264,632 | B2 | 9/2007 | Wright |
| 7,297,156 | B2 | 11/2007 | Nelson |
| 7,335,224 | B2 | 2/2008 | Ohlenschlaeger |
| 7,611,528 | B2 | 11/2009 | Goodson, IV |
| 7,632,298 | B2 | 12/2009 | Hijlkema et al. |
| 7,815,671 | B2 | 10/2010 | Wright et al. |
| 7,909,863 | B2 | 3/2011 | Hartley et al. |
| 7,942,924 | B1 | 5/2011 | Perez et al. |
| 7,959,661 | B2 | 6/2011 | Hijlkema et al. |
| 8,043,354 | B2 | 10/2011 | Greenberg et al. |
| 8,062,345 | B2 | 11/2011 | Ouellette et al. |
| 8,109,986 | B2 | 2/2012 | Styrc |
| 8,267,985 | B2 | 9/2012 | Garcia et al. |
| 8,449,599 | B2 | 5/2013 | Chau et al. |
| 9,220,617 | B2 | 12/2015 | Berra |
| 9,220,619 | B2 | 12/2015 | Berra |
| 2005/0049674 | A1 | 3/2005 | Berra et al. |
| 2006/0190070 | A1* | 8/2006 | Dieck ............ A61F 2/97 623/1.12 |
| 2006/0271153 | A1 | 11/2006 | Garcia et al. |
| 2007/0186933 | A1 | 8/2007 | Nicanor et al. |
| 2008/0264102 | A1 | 10/2008 | Berra |
| 2009/0030497 | A1 | 1/2009 | Metcalf et al. |
| 2009/0099637 | A1 | 4/2009 | Barthold et al. |
| 2009/0192585 | A1 | 6/2009 | Bloom et al. |
| 2009/0182405 | A1 | 7/2009 | De la Menardiere et al. |
| 2009/0192601 | A1 | 7/2009 | Rafiee et al. |
| 2009/0287299 | A1 | 11/2009 | Tabor et al. |
| 2009/0306761 | A1* | 12/2009 | Hebert ............ A61F 2/91 623/1.12 |
| 2010/0010617 | A1 | 1/2010 | Goodson, IV et al. |
| 2010/0152832 | A1 | 6/2010 | Hezi-Yamit |
| 2010/0249896 | A1 | 9/2010 | Sugimoto et al. |
| 2010/0324647 | A1* | 12/2010 | Rincon ............ A61F 2/962 623/1.11 |
| 2011/0251664 | A1* | 10/2011 | Acosta De Acevedo ............ A61F 2/954 623/1.11 |
| 2012/0010696 | A1 | 1/2012 | Greenberg et al. |
| 2012/0172969 | A1 | 7/2012 | Sugimoto et al. |
| 2012/0197379 | A1 | 8/2012 | Laske et al. |
| 2012/0259404 | A1 | 10/2012 | Tieu et al. |
| 2013/0085562 | A1* | 4/2013 | Rincon ............ A61F 2/95 623/1.11 |
| 2013/0253346 | A1 | 9/2013 | Griswold et al. |
| 2013/0274859 | A1* | 10/2013 | Argentine ............ A61F 2/95 623/1.12 |
| 2013/0274860 | A1 | 10/2013 | Argentine |
| 2013/0338787 | A1 | 12/2013 | Hopkins et al. |
| 2013/0338788 | A1 | 12/2013 | Hopkins et al. |
| 2013/0345789 | A1 | 12/2013 | Havel et al. |
| 2014/0142680 | A1 | 5/2014 | Laske et al. |
| 2014/0172067 | A1 | 6/2014 | Brown et al. |
| 2014/0180391 | A1* | 6/2014 | Dagan ............ A61N 1/0558 623/1.15 |
| 2014/0330299 | A1 | 11/2014 | Rosenbluth et al. |

FOREIGN PATENT DOCUMENTS

| | | |
|---|---|---|
| EP | 1440673 | 7/2004 |
| EP | 2266509 | 8/2013 |
| JP | 2011-519608 | 7/2011 |
| WO | 2000/065270 | 2/2000 |
| WO | 2008/098255 | 8/2008 |
| WO | PCT/US2009/039144 | 4/2009 |
| WO | 2009/098255 | 8/2009 |
| WO | WO2009/134801 | 11/2009 |

OTHER PUBLICATIONS

European Search Report for Application No. 10166254 dated Oct. 31, 2010, 2 pgs.
Extended European Search Report for Application No. 14275176.7 dated Jan. 8, 2015, 6 pgs.
Examiner's Report for Canadian Patent Application No. 2818268 dated Feb. 20, 2015, 3 pgs.
Final Office Action for Japanese Patent Application 2013-123785 dated Feb. 3, 2015, 4 pgs. including English translation.
First Office Action for Chinese Patent Application 201310232173.1 dated Feb. 25, 2015, 13 pgs. including English translation.
Office Action for U.S. Appl. No. 13/796,591 dated Apr. 2, 2015, 7 pgs.
Examination Report for European Patent Application 13171753.0 dated May 19, 2015, 6 pgs.
Examiner's Report for Canadian Patent Application No. 2,818,268 dated May 20, 2014, 2 pgs.
Office Action for Japanese Patent Application No. 2013-123785 dated Jun. 24, 2014, 7 pages including English translation.
Patent Examination Report for Australian Patent Application No. 2013206290 dated Jul. 7, 2014, 4 pages.
Reply to Official Letter dated Jan. 2, 2014 for European Patent Application No. 13171753.0 dated Jun. 17, 2014, 27 pages.
Response to Examiner's Report for Canadian Patent Application No. 2,818,268 filed Nov. 7, 2014, 6 pgs.
Response to Examiner's Report for Australian Patent Application 2013206290 filed Sep. 24, 2014, 8 pgs.
Notice of Acceptance for Australian Patent Application 2013206290 dated Nov. 13, 2014, 3 pgs.
Response to Office Action for Japanese Patent Application 2013-123785 filed Sep. 24, 2014, 9 pgs. including English translation.
Notice of Allowance for JP2013-123785 dated Oct. 6, 2015, 4 pgs.
Office Action dated Sep. 29, 2015 for Chinese patent application No. 201310232173.1, 12 pgs.
Office Action for U.S. Appl. No. 13/796,591 dated Nov. 25, 2015, 8 pgs.
Notice of Allowance for Canadian Patent Application 2818268 dated Nov. 2, 2015, 1 pg.
Third Office Action for Chinese Patent Application No. 20130232173.1 dated May 16, 2016, 14 pgs. including English translation.
Intention to Grant for corresponding European Application No. EP 13171753 .0 dated May 2, 2017, 58 pgs.
Notice of Allowance for corresponding Chinese Application No. CN 201310232173.1, dated Jan. 5, 2017, with English language translations, 2 pgs.

* cited by examiner

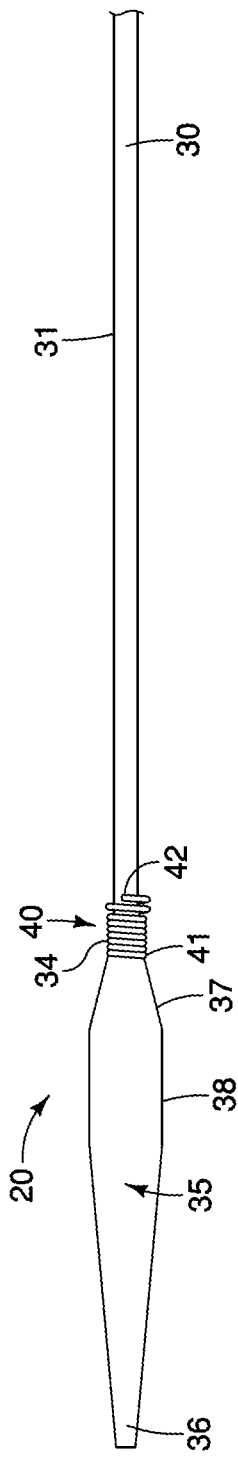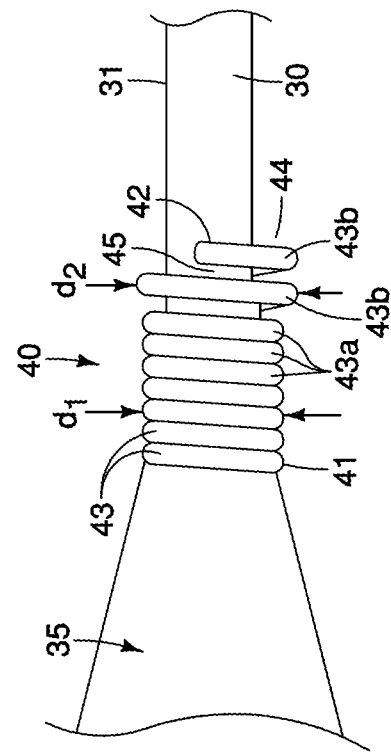

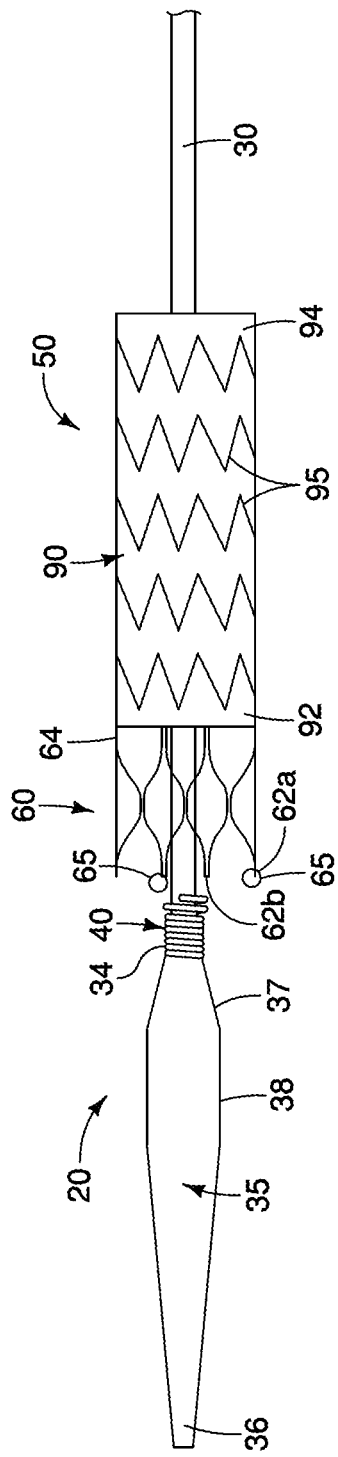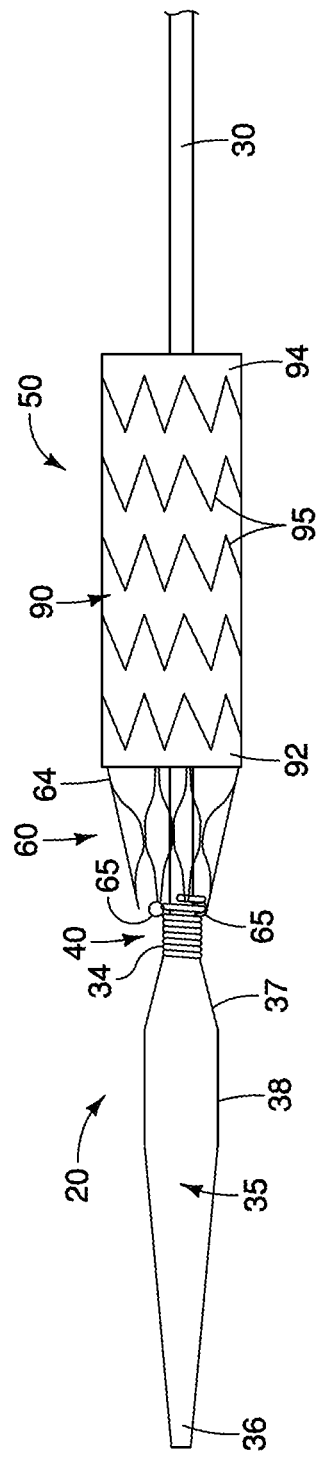

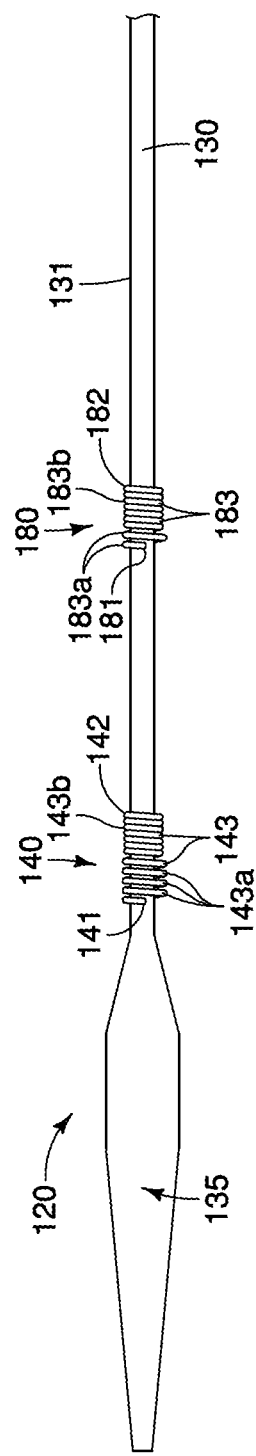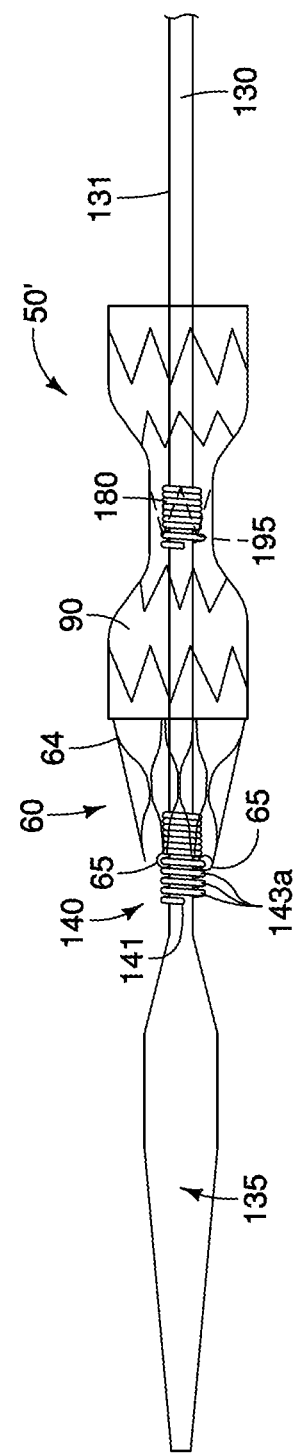

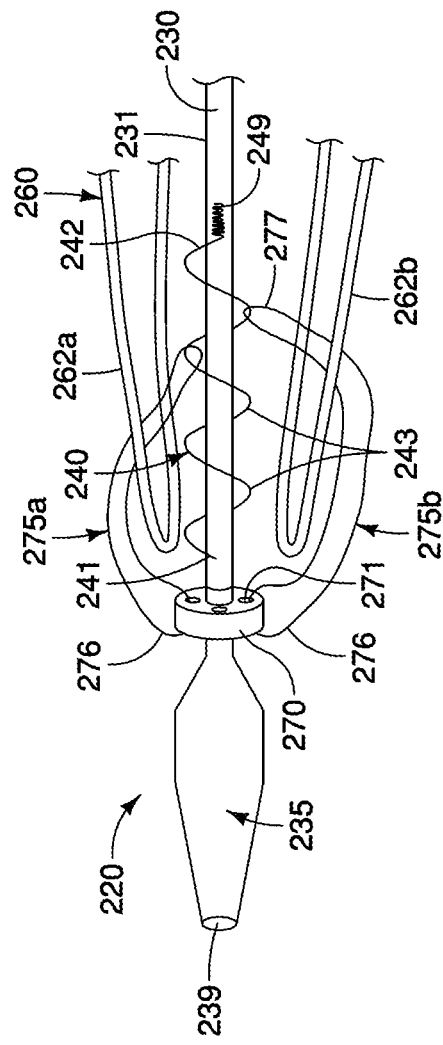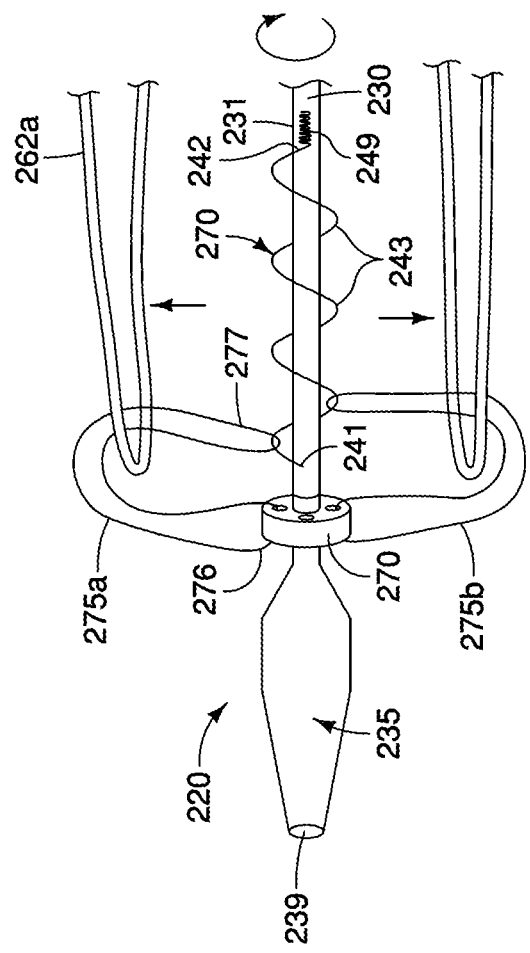

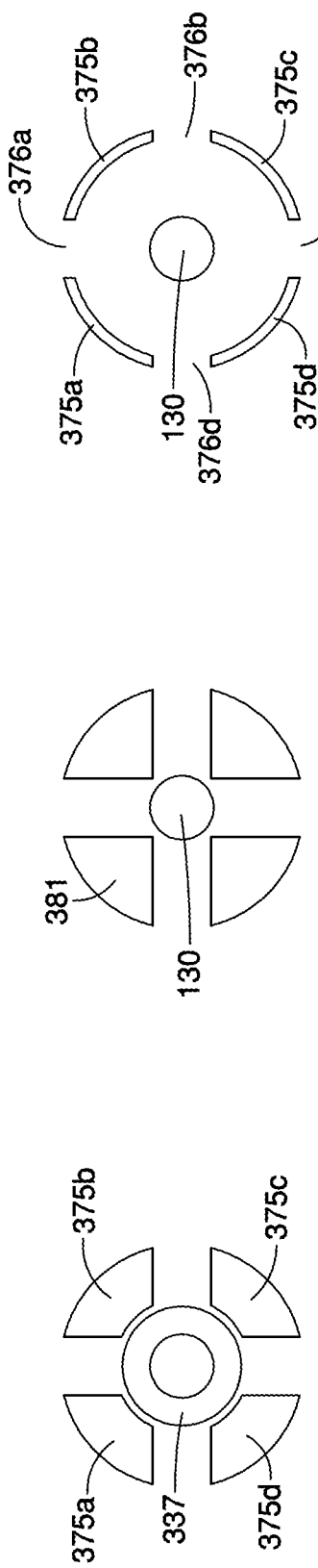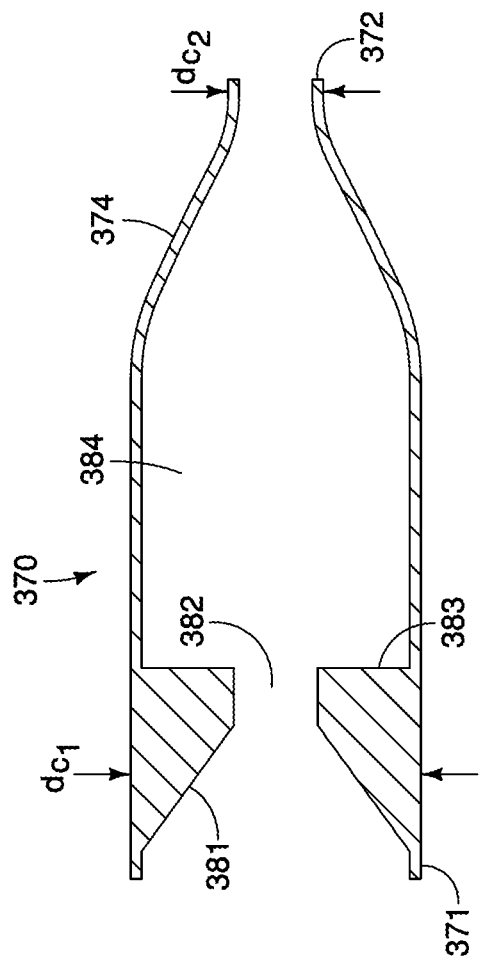

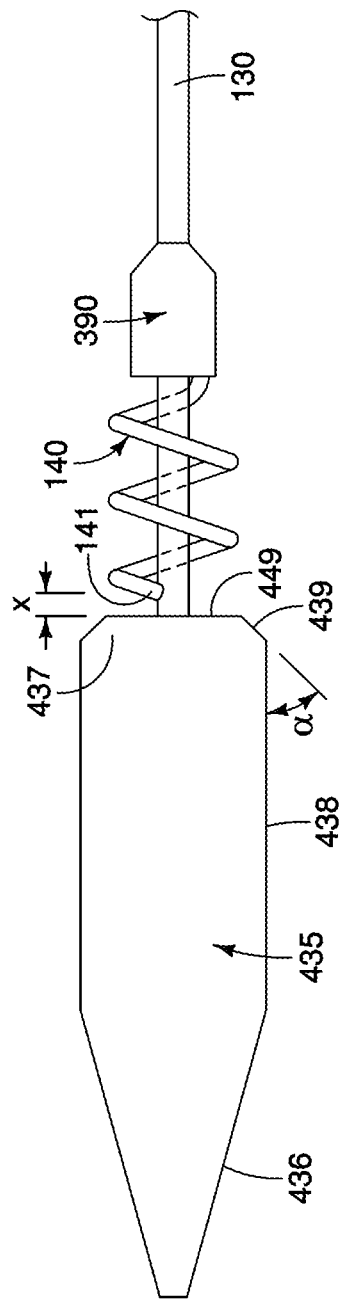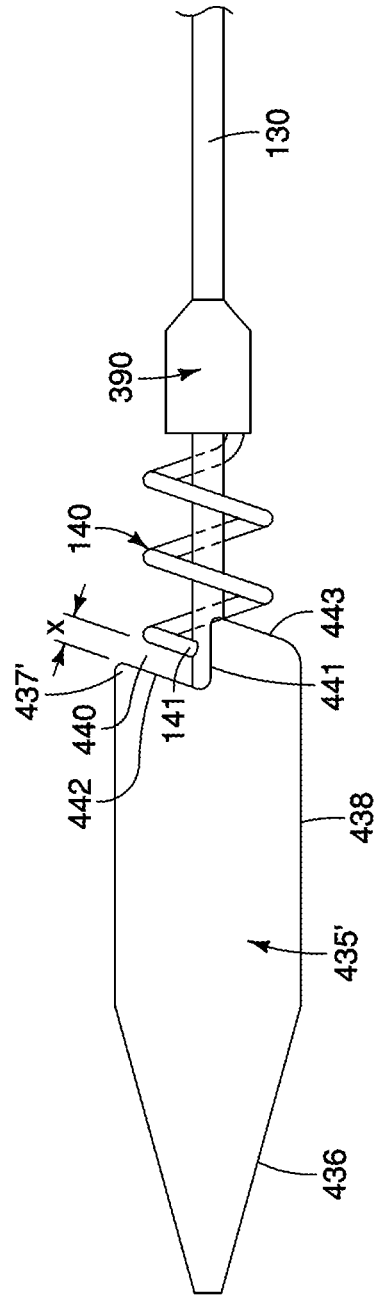

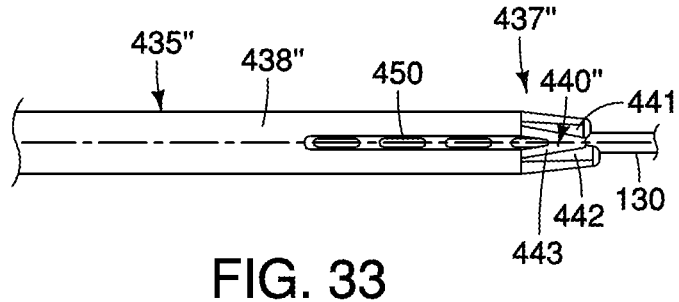
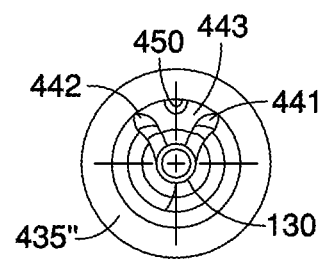
FIG. 33    FIG. 34
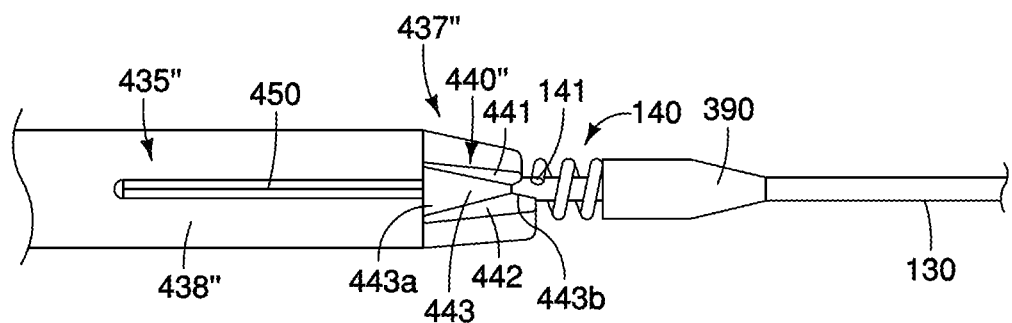
FIG. 35

SYSTEMS AND METHODS FOR DEPLOYING A PORTION OF A STENT USING AT LEAST ONE COILED MEMBER

PRIORITY CLAIM

The present patent document is a continuation application that claims the benefit of priority under 35 U.S.C. § 120 of U.S. patent application Ser. No. 14/867,791, filed Sep. 28, 2015, which is a divisional application that claims the benefit of priority under 35 U.S.C. § 121 of U.S. patent application Ser. No. 13/796,395, filed Mar. 12, 2013 (now U.S. Pat. No. 9,173,756), which claims the benefit of priority of U.S. Provisional Application Ser. No. 61/659,255, filed Jun. 13, 2012, and further claims the benefit of priority of U.S. Provisional Application Ser. No. 61/745,181, filed Dec. 21, 2012, all disclosures of which are hereby incorporated by reference in their entirety.

BACKGROUND

The present embodiments relate generally to apparatus and methods for treating medical conditions, and more specifically, to systems and methods for deploying a portion of a stent using at least one coiled member.

Stents may be inserted into an anatomical vessel or duct for various purposes. Stents may maintain or restore patency in a formerly blocked or constricted passageway, for example, following a balloon angioplasty procedure. Other stents may be used for different procedures, for example, stents placed in or about a graft have been used to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they can have characteristics of both types of stents. Self-expanding stents may be delivered to a target site in a compressed configuration and subsequently expanded by removing a delivery sheath, removing trigger wires and/or releasing diameter reducing ties. With self-expanding stents, the stents expand primarily based on their own expansive force without the need for further mechanical expansion. In a stent made of a shape-memory alloy such as nitinol, the shape-memory alloy may be employed to cause the stent to return to a predetermined configuration upon removal of the sheath or other device maintaining the stent in its predeployment configuration.

When trigger wires are used as a deployment control mechanism, the trigger wires may releasably couple the proximal and/or distal ends of a stent or stent-graft to a delivery catheter. Typically, one or more trigger wires are looped through a portion of the stent near a vertex of the stent. For example, trigger wires may be used to restrain a "Z-stent" or Gianturco stent comprising a series of substantially straight segments interconnected by a series of bent segments. The trigger wires may be disposed through, and pull upon, the bent segments to pull the stent closely against the delivery catheter.

Trigger wires also may be used in conjunction with different stent designs, such as cannula-cut stents having relatively acute or pointed bends. The designs of cannula-cut stents may facilitate compression of the stent to a relatively small delivery profile due to the tight bends of the apices. With such stents, the trigger wires may be looped around one or more vertices formed beneath the proximal and/or distal apices, e.g., a location where an individual apex splits into two separate strut segments.

If trigger wires are threaded through the vertices of such cannula-cut stents, the trigger wires may become crimped at the vertices during compression of the stent to a reduced diameter delivery profile. If the trigger wires are crimped between the strut segments, the trigger wires and/or stent segments may become damaged during delivery, particularly for nickel-titanium stents that may be sensitive to surface imperfections. Furthermore, when compressing a cannula-cut stent having relatively acute bends to a significantly reduced radial profile, barbs disposed near the apices of the stent may become entangled with the stent struts and/or the trigger wires. Still further, in some instance, trigger wires may require a relatively high deployment force when being retracted, and the provision of multiple trigger wires may add to the profile of the delivery system.

SUMMARY

The present embodiments provide systems and methods for deploying at least a portion of a stent. In one embodiment, the system comprises a cannula having an outer surface, and at least one coiled member having proximal and distal ends and a plurality of turns disposed therebetween. One of the proximal and distal ends of the coiled member is secured to the outer surface of the cannula, and the other of the proximal and distal ends of the coiled member is unsecured relative to the outer surface of the cannula. A portion of a stent is looped around the unsecured end of the coiled member and disposed within spacing between adjacent turns of the coiled member. Rotation of the cannula subsequently causes the portion of the stent to disengage from the coiled member.

In one embodiment, the distal end of the coiled member is secured to the outer surface of the cannula and the proximal end of the coiled member is unsecured relative to the outer surface of the cannula. In this example, a portion of the stent is looped around the proximal end of the coiled member and further is disposed within spacing between adjacent proximal turns of the coiled member in the delivery state.

In an alternative embodiment, the proximal end of the coiled member is secured to the outer surface of the cannula and the distal end of the coiled member is unsecured relative to the outer surface of the cannula, and a portion of the stent is looped around the distal end of the coiled member and further is disposed within spacing between adjacent distal turns of the coiled member in the delivery state. In this embodiment, a distal series of turns of the coiled member may be spaced apart further from one another relative to spacing between a proximal series of turns. Further, a first diameter at the proximal end of the coiled member permits attachment to the outer surface of the cannula, while a second diameter at the distal end of the coiled member is greater than the first diameter and there is a gap disposed between the distal end of the coiled member and the outer surface of the cannula.

In one embodiment, first and second coiled members are provided and are longitudinally spaced apart from one another along a length of the cannula. In this example, the first coiled member engages a first stent portion in the delivery state and the second coiled member engages a second stent portion in the delivery state. The first coiled member may comprise a greater number of turns that are unsecured relative to the cannula than the second coiled member, thereby enabling the second stent portion to disengage from the second coiled member before the first stent portion disengages from the first coiled member when the cannula is rotated in a uniform direction.

In various embodiments, a ring portion may extend from the stent and is dimensioned to be accommodated within the spacing between adjacent turns of the coiled member in the delivery state. The ring portion may comprise a wall thickness that is less than a wall thickness of other regions of the stent, thereby permitting twisting of the ring portion in a circumferential direction to facilitate coupling of the stent to the coiled member.

In a further alternative embodiment, at least one suture loop comprises a proximal region that is coupled to the cannula, and a distal region that is retained within one of the plurality of turns of the coiled member in the delivery state. The suture loop is further coupled around a portion of a stent in the delivery state. Rotation of the cannula causes longitudinal movement of the distal region of the suture loop relative to the proximal region of the suture loop, thereby varying the slack in the suture loop and varying expansion of the portion of the stent that is coupled to the suture loop.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 1 is a side view of a first embodiment of an apparatus for deploying a portion of a stent using at least one coiled member.

FIG. 2 is an enlarged view of the coiled member of FIG. 1.

FIGS. 4-5 are side views depicting coupling of the stent-graft of FIG. 3 to the apparatus of FIGS. 1-2.

FIG. 14 is a side view of an alternative embodiment of an apparatus for deploying stent portions using first and second coiled members.

FIG. 15 is a side view depicting coupling of a stent-graft to the apparatus of FIG. 14.

FIGS. 19-20 are side views of yet a further alternative embodiment of an apparatus for deploying a portion of a stent using at least one coiled member in a delivery state and a partially deployed state, respectively.

FIGS. 23A-23C are, respectively, cross-sectional views of the protective cage of FIG. 21 as taken along lines A-A, B-B and C-C.

FIG. 24 is a side-sectional view of the protective cage of FIG. 21.

FIG. 29 is a side view of an alternative atraumatic tip and coiled member arrangement.

FIG. 30 is a side view of a further alternative atraumatic tip and coiled member arrangement.

FIGS. 33-35 are, respectively, a side view of a further alternative atraumatic tip for use with a coiled member arrangement, and end view of FIG. 33, and a side illustration of the atraumatic tip of FIGS. 33-34 with a coiled member disposed in the vicinity.

DETAILED DESCRIPTION OF THE PREFERRED EMBODIMENTS

Figure 3:
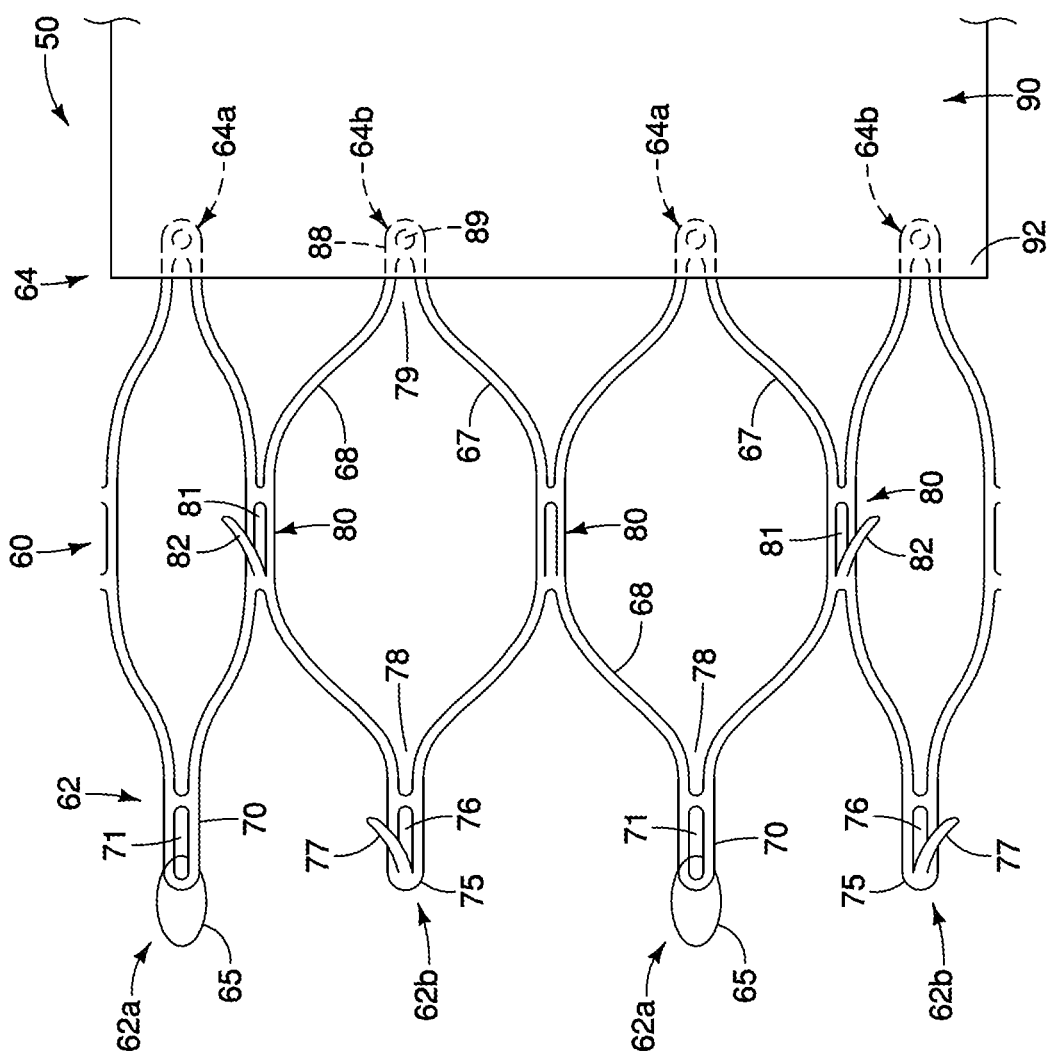
FIG. 3 depicts an exemplary stent-graft having a portion that may be deployed using the coiled member of FIGS. 1-2.

In the present application, the term "proximal" refers to a direction that is generally closest to the heart during a medical procedure, while the term "distal" refers to a direction that is furthest from the heart during a medical procedure.

Referring to FIGS. 1-2, a first embodiment of an apparatus 20 is shown for deploying a portion of a stent using at least one coiled member. The apparatus 20 generally comprises a cannula 30 having an outer surface 31, and at least one coiled member 40 having a region that is secured to the outer surface 31 of the cannula 30.

The cannula 30 may be incorporated as part of a broader stent or stent-graft delivery system, and may span a longitudinal length in which a distal segment extends outside of a patient's body, and a proximal segment 34, including the coiled member 40, is delivered towards a target site inside of a patient's body. The cannula 30 may be used as an inner cannula, to the extent that one or more outer cannulas or sheaths are disposed coaxially over the cannula 30. For example, a stent-graft may be disposed over an exterior surface of the cannula 30 and within one or more outer cannulas or sheaths, thereby encompassing the stent-graft during a delivery stage.

The cannula 30 may comprise a tubular member having a lumen sized to allow the cannula 30 to be advanced over a wire guide during delivery. A proximal region of the cannula 30 may be integrally formed with, or externally coupled to, an atraumatic tip 35. The atraumatic tip 35 may comprise proximal and distal regions 36 and 37, respectively, and a central region 38 disposed therebetween. The proximal and distal regions 36 and 37 comprise a smaller outer diameter relative to the central region 38, with a first taper allowing for a smooth transition between the proximal region 36 and the central region 38, and a second taper allowing for a smooth transition between the distal region 37 and the central region 38.

The coiled member 40 comprises a proximal end 41, a distal end 42, and a plurality of turns 43 disposed therebetween, as shown in FIGS. 1-2. In this non-limiting example, the proximal end 41 of the coiled member 40 is secured to the outer surface 31 of the cannula 30 using a suitable mechanism, such as a solder, weld, mechanical attachment, friction fit, crimp, or combination of these or other techniques and mechanisms. Accordingly, the proximal end 41 of the coiled member 40 cannot move relative to the outer surface 31 of the cannula 30. The proximal end 41 of the coiled member 40 comprises a first diameter $d_1$, which may be approximately the same diameter, or slightly greater than, an outer diameter of the cannula 30.

The distal end 42 of the coiled member 40 is unsecured relative to the outer surface 31 of the cannula 30, as shown in FIGS. 1-2. The distal end 42 of the coiled member 40 may comprise a second diameter $d_2$, which is greater than the first diameter $d_1$ of the proximal end 41 of the coiled member 40. There is a separation or gap 44 between the distal end 42 of the coiled member 40 and the outer surface 31 of the cannula 30, as best seen in FIG. 2.

The plurality of turns 43 are divided into a proximal series of turns 43a, which have the first diameter $d_1$, and a distal series of turns 43b, which have the second diameter $d_2$. The proximal series of turns 43a may be disposed in close proximity or abutting one another, as depicted in FIG. 2. By contrast, the distal series of turns 43b may be spaced apart from one another a greater distance than the proximal series of turns 43a. In FIG. 2, the distal series of turns 43b are spaced apart a predetermined distance denoted by spacing 45. As will be described further in FIGS. 4-5 below, a portion of a stent 60 may be coupled to at least one of the distal series of turns 43b, and secured within the spacing 45 between adjacent distal turns.

The exemplary coiled member 40 may be formed from stainless steel, nitinol, titanium, or other suitable biocompatible materials. If manufactured from nitinol, the unsecured end of the coiled member may be heat-set so that it contracts around the outer surface 31 of the cannula 30 when disposed within the body, thereby reducing the likelihood of the coiled member 40 snagging the stent 60 or other components. In one example, the coiled member 40 is formed from a material that has radiopaque properties.

Referring now to FIG. 3, an exemplary stent-graft 50, having a proximally-located stent 60 coupled to a graft material 90, may be deployed in a controlled manner using the coiled member 40 of FIGS. 1-2, as shown further in the exemplary coupling sequence of FIGS. 4-5 below. In this non-limiting embodiment, the stent 60 may be manufactured from a continuous cylinder into which a pattern may be cut by a laser or by chemical etching to produce slits in the wall of the cylinder. The resulting structure may then be heat set to give it a desired final configuration. As shown in FIG. 3, the final configuration may include a shape having a series of proximal apices and a series of distal apices. A proximal end 62 of the stent 60 may comprise multiple adjacent proximal apices 62a and 62b, while a distal end 64 of the stent 60 may comprise multiple adjacent distal apices 64a and 64b, as shown in FIG. 3.

In FIG. 3, at least one pair of adjacent, proximal apices 62a and 62b may comprise different features. For example, as shown in FIG. 3, a first proximal apex 62a may comprise an end region 70 having a bore 71 formed therein, wherein the bore 71 is configured to receive a suture loop 65, as explained further below. A second, adjacent proximal apex 62b may comprise an end region 75 having an integral barb 77 formed therein, as shown in FIG. 3. The barb 77 may be formed by laser cutting a desired barb shape into the end regions 75. A slit 76 therefore is formed into each end region 75 after the desired barb shape is formed, as shown in FIG. 3. Once the desired barb shape is cut, a main body of the barb 77 may be bent in a radially outward direction with respect to the end region 75. The angle may comprise any acute angle, or alternatively may be substantially orthogonal or obtuse. If desired, the barb 77 may be sharpened, for example, by grinding the tip of the barb, to facilitate engagement at a target tissue site.

Referring still to FIG. 3, the stent 60 may comprise at least one strut segment disposed between the proximal and distal apices. For example, multiple angled strut segments may be disposed between a first proximal apex 62a and a corresponding distal apex 64a, and an identical set of angled strut segments may be disposed between an adjacent, second proximal apex 62b and a corresponding distal apex 64b. By way of example, a first proximal apex 62a extends distally and splits into first and second angled strut segments 67 and 68, respectively, thereby forming a proximal vertex 78, as shown in FIG. 3. In a compressed state, the first and second angled strut segments 67 and 68 may be compressed such that they are substantially parallel to one another. Similarly, each distal apex 64a and 64b may extend in a proximal direction and split into the first and second angled strut segments 67 and 68, respectively, thereby forming a distal vertex 79. A first angled strut segments 67 may meet with an adjacent second angled strut segment 68, thereby forming a transition region 80. In this manner, the stent 60 may be formed into a continuous, generally cylindrical shape, as shown in FIG. 3.

Expansion of the stent 60 is at least partly provided by the angled strut segments 67 and 68, which may be substantially parallel to one another in a compressed state, but may tend to bow outward away from one another in the expanded state shown in FIG. 3. The stent 60 may be formed from any suitable material, such as a laser-cut nitinol cannula. If manufactured from nitinol, the stent 60 may be inclined to assume the expanded state shown in FIG. 3 upon removal of a delivery sheath or engagement with the coiled member 40, as explained in FIGS. 4-5 below.

Each transition region 80 may comprise a larger surface area relative to the angled segments, since the transition regions are composed substantially of multiple different angled segments 67 and 68. The stent 60 may comprise at least one barb 82 disposed in at least one of the transition regions 80. The barb 82 may be formed integrally, as part of the strut, or may comprise an external barb that is adhered to a surface of the transition regions 80. As shown in FIG. 3, multiple integral barbs 82 are provided. Like the barbs 77 noted above, the barbs 82 may be formed by laser cutting a desired barb shape into the transition regions 80. A slit 81 therefore is formed into the transition region 80 after the desired barb shape is formed, as shown in FIG. 3. Since the transition regions 80 may comprise an increased surface area relative to other regions of the stent 60, it may be easier to perforate portions of the transition regions 80 without adversely affecting the structural integrity of the stent. Once the desired barb shape is cut, a main body of the barb 82 may be bent in an outward direction at any angle with respect to the transition region 80 and optionally may be sharpened to facilitate engagement at a target tissue site.

Each of the distal apices 64a and 64b may comprise an end region 88 having a bore 89 formed therein, as shown in FIG. 3. The distal end 64 of the stent 60 may be coupled to a proximal end 92 of the graft material 90. The distal apices 64a and 64b may be coupled to the graft material, for example, using one or more sutures that are looped through the graft material and the bores 89 of the stent 80. In this manner, the stent 60 may be used as an attachment stent for endovascular graft fixation. For example, the graft material 90 may overlap with an aneurysm to seal off fluid flow into the aneurysm, while the proximal end 62 of the stent 60 may extend in a proximal direction away from the graft material, e.g., to engage a healthy portion of a vessel wall away from a diseased portion of the aneurysm. As will be apparent, one or more additional stents may be coupled to an inner or outer surface of the graft material 90, i.e., at a location distal to the stent 60, to help maintain patency throughout the graft material. While multiple exemplary zig-zag stents 95 are shown coupled to the graft material 90 between the proximal and distal ends 92 and 94 of the graft material 90 in FIGS. 4-5, it will be apparent than any shape of stent may be used, and such stents may be coupled to either the inner or outer surfaces of the graft material 90.

The stent 60 has a reduced diameter delivery state so that it may be advanced to a target location within a vessel or duct. The stent 60 also has an expanded deployed state to apply a radially outward force upon at least a portion of a vessel or duct, e.g., to maintain patency within a passageway, or to hold open the lumen of a graft. In the expanded state, fluid flow is allowed through a central lumen of the stent 60. Further, the struts of the stent 60 may comprise a substantially flat wire profile or may comprise a rounded profile. As best seen in FIG. 3, the struts of the stent 60 generally comprise a flat wire profile.

The stent 60 may be manufactured from a super-elastic material. Solely by way of example, the super-elastic material may comprise a shape-memory alloy, such as a nickel titanium alloy (nitinol). If the stent 60 comprises a self-expanding material such as nitinol, the stent may be heat-set into the desired expanded state, whereby the stent 60 can assume a relaxed configuration in which it assumes the preconfigured first expanded inner diameter upon application of a certain cold or hot medium. Alternatively, the stent 60 may be made from other metals and alloys that allow the stent 60 to return to its original, expanded configuration upon deployment, without inducing a permanent strain on the material due to compression. Solely by way of example, the stent 60 may comprise other materials such as stainless steel, cobalt-chrome alloys, amorphous metals, tantalum, platinum, gold and titanium. The stent 60 also may be made from non-metallic materials, such as thermoplastics and other polymers.

While one exemplary stent 60 is shown in FIG. 3 and described in FIGS. 4-5 below, various alternative stent configurations may be used in conjunction with the coiled member 40 of FIGS. 1-2. Moreover, the stent may be deployed alone, or as part of a stent-graft system, as depicted herein.

Referring now to FIGS. 4-5, an exemplary coupling of the stent-graft 50 of FIG. 3 to the deployment apparatus of FIGS. 1-2 is shown and described. The stent-graft 50 has an uncoupled state in which the stent-graft 50 is positioned coaxially over the cannula 30 with the proximal end 62 of the stent 60 in longitudinal proximity relative to the distal end 42 of the coiled member 40, as shown in FIG. 4. During assembly, the suture loops 65 that are coupled to the proximal apices 62a of the stent 60 are threaded around the distal end 42 of the coiled member 40 one at a time, preferably until all of the suture loops 65 are coupled to the coiled member 40. Such coupling may be achieved by rotating the cannula 30 in a clockwise direction until the proximal end 62 of the stent 60 is sufficiently compressed in a radially inward direction, as depicted in FIG. 5. It should be noted that the gap 44 between the distal end 42 of the coiled member 40 and the outer surface 31 of the cannula 30 permits positioning of the suture loops 65 around the distal series of turns 43b.

The suture loops 65 are further accommodated within the spacing 45 between the distal series of turns 43b. The suture loops 65 preferably are coupled to the coiled member 40 in a manner in which at least one suture loop 65 is positioned around at least one full turn of the distal series of turns 43b, and preferably around at least 1.5 turns at the distal end 42 of the coiled member 40, thereby reducing the likelihood of inadvertent uncoupling of the suture loops 65 from the coiled member 40.

The coupling shown in FIG. 5 secures the stent 60 to the cannula 30 via the coiled member 40 in a manner that may subsequently facilitate insertion of the subassembly comprising the cannula 30 and the stent-graft 50 into an outer sheath. As will be apparent, the outer sheath is configured to radially restrain other regions of the stent-graft 50 for delivery to a target site within a patient's anatomy.

In this embodiment, the suture loops 65 are coupled to every other proximal apex 62a to restrain the stent 60 during delivery. The suture loops 65 are not coupled to the second proximal apices 62b, which comprise the barbs 77. By restraining the alternating proximal apices 62a using the suture loops 65 coupled to the coiled member 40, the adjacent second proximal apices 62b also may be indirectly pulled in a radially inward direction during delivery. The configuration of the stent 60, and in particular the angled segments 67 and 68 that meet up at transition regions 80, facilitates the indirect compression of the adjacent second proximal apices 62b. Since only selected ones of the proximal apices are restrained during delivery, the number of suture loops 65 may be reduced. Moreover, since the barbs 77 are only disposed on every other apex, barb entanglement may be reduced or eliminated.

An introducer, similar to that described in PCT application WO98/53761, entitled "A Prosthesis and a Method and Means of Deploying a Prosthesis," which is incorporated herein by reference in its entirety, may be used to deploy the stent-graft 50. PCT application WO98/53761 describes a deployment system for an endoluminal prosthesis whereby the prosthesis is radially compressed onto a delivery catheter and is covered by an outer sheath. To deploy the system, the operator slides or retracts the outer sheath over the delivery catheter, thereby exposing the prosthesis. The prosthesis expands outwardly upon removal of the sheath. The operator can directly manipulate the sheath and the delivery catheter, which provides the operator with a relatively high degree of control during the procedure. However, in the current embodiments, trigger wires and any of their associated sleeves would not be necessary to deploy the stent-graft 50. Rather, the cannulas 30, 130, 130' and 230 and the coiled members 40, 140 and 180 of the present embodiments may be incorporated as part of the deployment system with the stent-graft 50 being positioned coaxially between the cannula 30 and the outer sheath. A mechanism, such as a pin vise, may be employed to prevent inadvertent rotation of the cannula 30 prior to the intended rotation as described in the present application.

In the present embodiments, a wire guide may be advanced to the target site, and the cannula 30 may be advanced over the wire guide to position the apparatus 20 at the desired location in proximity to the target site, with the atraumatic tip 35 reducing the likelihood of injury to bodily passageways during delivery. The outer sheath is disposed over the cannula 30 and the stent-graft 50 during insertion to the target site. Upon proper positioning at the target site using a desired imaging modality, the outer sheath is then retracted to expose at least a portion of the stent 60.

When the stent 60 is at least partially exposed, and it is desirable to deploy the proximal end 62 of the stent 60, the cannula 30 may be rotated in a counter-clockwise direction until the suture loops 65 are uncoupled from the coiled member 40, i.e., in a reverse manner from which the suture loops 65 were coupled to the coiled member 40. The stent 60 then may be deployed as shown in FIG. 4, and the remainder of the stent-graft 50 may be deployed by further retraction of the outer sheath or actuation of any other devices that are radially constraining the remainder of the stent-graft 50. As will be explained further in FIGS. 14-15 below, a plurality of coiled members may be used to selectively deploy multiple stent portions of the stent-graft 60.

Advantageously, the proximal end 62 of the stent 60 is radially restrained without the use of convention trigger wires that span a full longitudinal length of the delivery system. Accordingly, the radial profile of the delivery system may be reduced without the provision of multiple trigger wires and one or more associated sleeves to house the trigger wires, thereby reducing packing density of the system. Moreover, deployment may be simplified as reduced deployment forces are expected to be needed relative to the use of conventional trigger wires.

As a further advantage, deployment of the stent 50 using the apparatus 20 comprising at least one coiled member 40 may allow for more precise positioning of the stent 50. In particular, deployment using the coiled member 40 may provide a more controlled unwinding of the associated portion of the stent 50, whereas the release of conventional trigger wires may require higher deployment forces that can cause a portion of the stent to jump longitudinally, thereby potentially deploying the stent offset from the intended target site.

Figure 7:
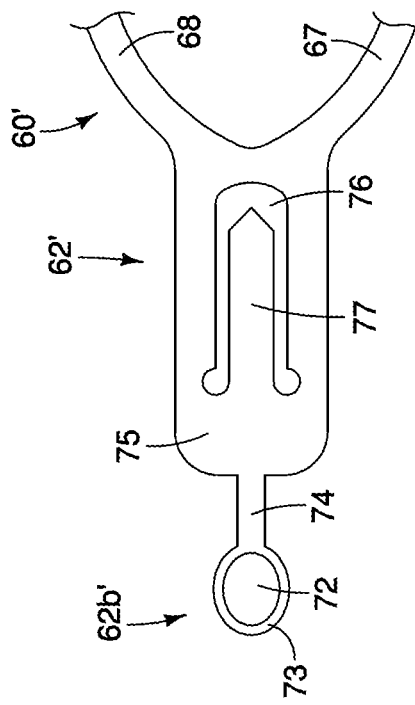
FIGS. 7-8 are side views depicting twisting of a portion of the proximal apex of the stent of FIG. 6.
Figure 8:
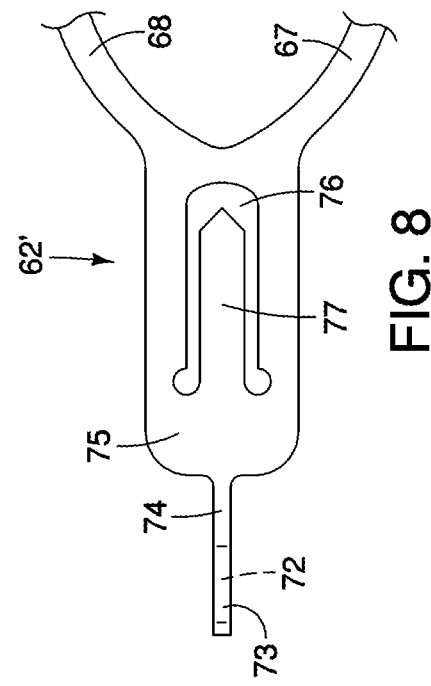
Figure 6:
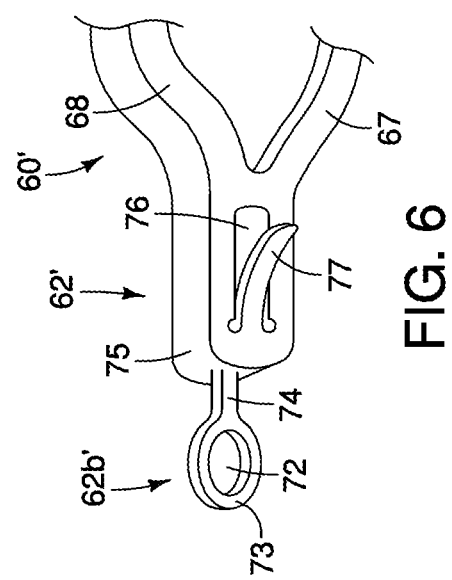
FIG. 6 is a perspective view of a proximal apex of a stent that may be coupled to a coiled member.

Referring now to FIGS. 6-8, a portion of an alternative stent 60' is described for use with the apparatus 20 comprising at least one coiled member 40 as described in FIGS. 1-2 and FIGS. 4-5. The alternative stent 60' is similar to the stent 60 of FIG. 3, with a main exception that an alternative proximal end 62' comprises at least one alternative proximal apex 62b' having an region comprising an eyelet 72.

The eyelet 72 may be formed within a ring portion 73 that is disposed at the proximal end of a proximal extension segment 74. The proximal extension segment 74 extends in a proximal direction away from the end region 75 having the integral barb 77, as shown in FIGS. 6-8.

In accordance with one aspect, the ring portion 73 and the proximal extension segment 74 comprise a wall thickness that is less than a wall thickness of the end region 75 having the integral barb 77, as best seen in FIG. 6. Advantageously, the reduced wall thickness of the ring portion 73 and the proximal extension segment 74 allows at least the ring portion 73 to twist in a circumferential direction to facilitate loading of the proximal apex 62' around the coiled member 40. In the example shown, the ring portion 73 twists in a circumferential direction about 90 degrees between a first state shown in FIG. 7 and a second state shown in FIG. 8. As will be apparent, the ring portion 73 may twist greater or less than 90 degrees, and the exemplary depiction between the states of FIGS. 7 and 8 is not intended to be limiting. Moreover, at least a portion of the proximal extension segment 74 may twist in the circumferential direction. The proximal extension segment 74 may twist a greater amount proximally since it is further from attachment from the end region 75 having the greater wall thickness.

As another advantage, the proximal extension segment 74 provides longitudinal separation of the ring portion 73 housing the eyelet 72 from the end region 75 having the integral barb 77. Accordingly, when the eyelet 72 is threaded around the coiled member 40, the proximal extension segment 74 provides a longitudinal spacing that reduces the likelihood of entanglement between the coiled member 40 and the integral barb 77 of the end region 75.

In the example of FIGS. 6-8, the ring portion 73 and the proximal extension segment 74 may be integrally formed with the end region 75. If the stent 60' is formed from nitinol or a similar material, the superelastic properties of such material can facilitate circumferential twisting of the ring portion 73 between the first and second states shown in FIGS. 7 and 8.

The alternative proximal apex 62b' shown in FIGS. 6-8 may be provided on each and every proximal apex of the stent 60'. Alternatively, the alternative proximal apex 62b' may be provided on fewer than all of the proximal apices of the stent 60', and the remaining proximal apices may be provided with only barbs, e.g., as depicted by the proximal apices 62b in FIG. 3 above, or the proximal apices may comprise other features.

Figure 9:
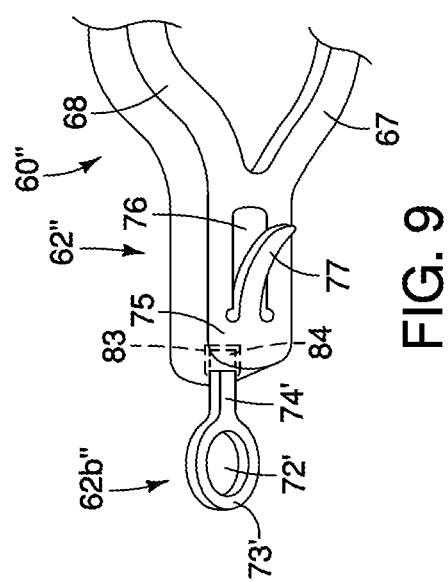
FIG. 9 is a perspective view of an alternative proximal apex of a stent that may be coupled to a coiled member.

Referring now to FIG. 9, a further alternative stent 60" has a proximal end 62" having at least one proximal apex 62b", which is similar to the proximal apex 62b' of FIGS. 6-8, with a main exception that an alternative ring portion 73' having an eyelet 72' and proximal extension segment 74' are formed separately from the end region 75. In this example, a bore 83 is formed at a proximal edge of the end region 75 at a location spaced proximally away from the integral barb 77, as shown in FIG. 9. A distal portion 84 of the proximal extension segment 74' is sized to be received within the bore 83 of the end region 75. The distal portion 84 of the proximal extension segment 74' then may be secured, e.g., using a solder or weld, within the bore 83 of the end region 75, forming the proximal apex 62b" shown in FIG. 9. In this alternative embodiment, the ring portion 73' and the proximal extension segment 74' optionally may be formed of a different material, such as a more flexible material, relative to the remainder of the stent 60".

Figure 10:
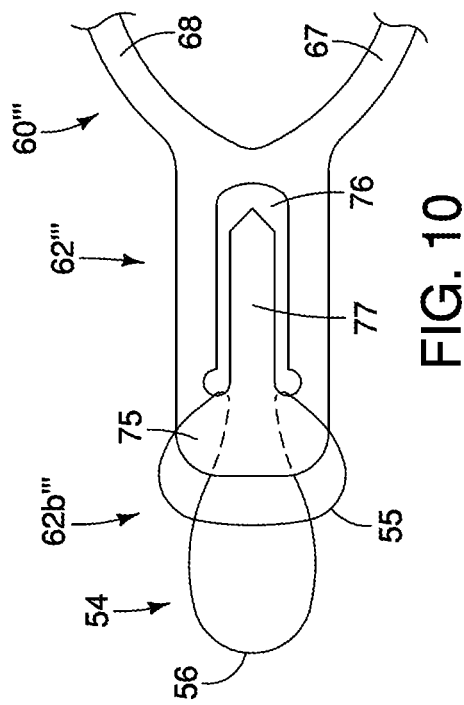
FIGS. 10-11 are side views depicting a further alternative proximal apex of a stent that may be coupled to a coiled member.
Figure 11:
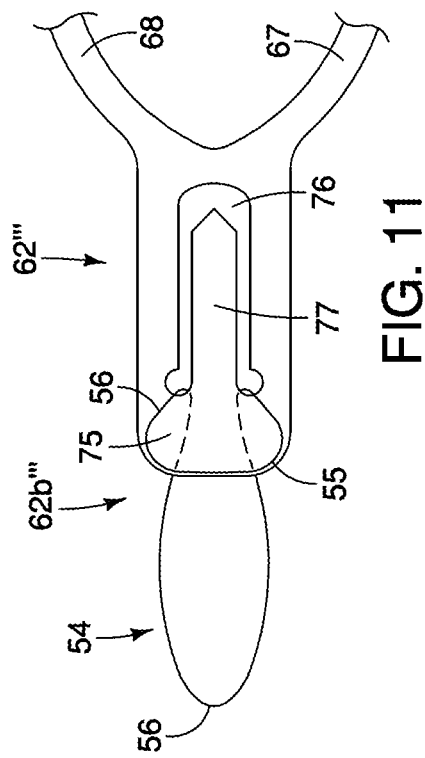

Referring now to FIGS. 10-11, a further alternative stent 60''' has a proximal end 62''' having at least one proximal apex 62b'''. In this example, a wire loop 54 is coupled to the end region 75 having the integral barb 77 by winding the wire loop 54 around a portion of the slit 76 formed into the end region 75. The wire loop 54 may be wound securely by placing a first loop portion 55 under the end region 75, then around the barb 77, and folding over proximally through the slot 76, as shown in FIG. 10. Then, a second loop portion 56, which preferably is larger than the first loop portion 55 and disposed primarily proximally to the first loop portion 55, may be pulled in a proximal direction as depicted in FIG. 11. By pulling the second loop portion 56 proximally, the first loop portion 55 shortens and tightens around the end region 75, as shown in FIG. 11. Optionally, a solder may be applied to hold the first loop portion 55 tightly around the end region 75. The resulting structure comprises the second loop portion 56 extending proximally away from the end region 75 in a manner such that the second loop portion 56 can be wound around the coiled member 40 of FIGS. 1-2 and 4-5, in the manner generally described above with respect to the suture loop 65.

Advantageously, the wire loop 54 may be formed from a flexible material. If formed from nitinol or a similar material, the superelastic properties of such material can facilitate circumferential twisting of the second loop portion 56 between the first and second states shown in FIGS. 7 and 8, thereby facilitating engagement around the coiled member 40. Moreover, the wire loop 54 may be considerably thinner than the end region 75 to facilitate engagement around the coiled member 40, e.g., by permitting twisting of the second loop portion 56 as needed during loading, and also by having a reduced thickness wire loop that can easily fit within the gap 44 and spacing 45 around the coiled member 40, as explained above.

Figure 13:
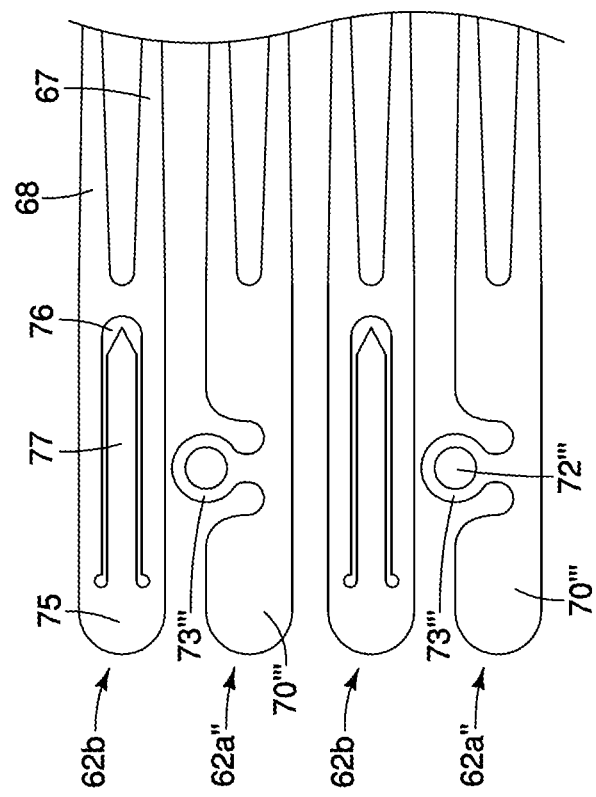
FIG. 13 is a side view of yet further alternative proximal apices of a stent that may be coupled to a coiled member.
Figure 12:
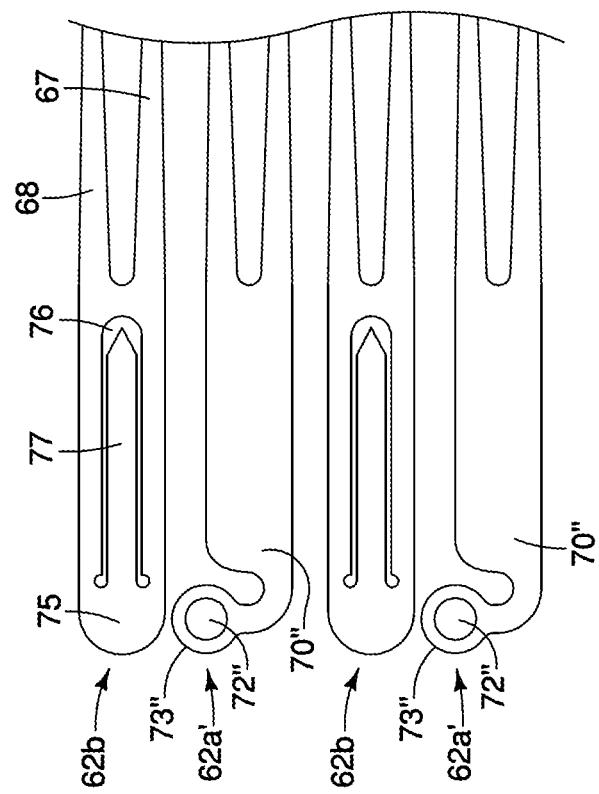
FIG. 12 is a side view of further alternative proximal apices of a stent that may be coupled to a coiled member.

Referring now to FIGS. 12-13, further alternative proximal ends of exemplary stents, suitable for deployment via the apparatus 20 having the coiled member 40, are shown and described. In FIG. 12, an alternative proximal region of a stent comprises alternating proximal apices 62a' and 62b. The proximal apices 62b are substantially identical to the proximal apices 62b described above in FIG. 3. However, the proximal apices 62a' differ from the proximal apices 62a of FIG. 3 by replacing the end region 70 having the bore 71 that is configured to receive the suture loop 65 with an alternative end region 70" that has an integral eyelet 72" within a ring portion 73". In the embodiment of FIG. 12, the ring portion 73" may be disposed at the proximal end of the end region 70". The ring portion 73" then may be cut into this pattern in a manner integral with the remainder of the stent, e.g., by laser cutting a cannula. The ring portion 73" subsequently may be bent radially inward at a desired angle, such as between 45 and 90 degrees, and then heat-set into the bent position to facilitate engagement with the coiled member 40 described above.

The alternative embodiment of FIG. 13 is similar to FIG. 12, with the exception that alternative proximal apices 62a''' comprise end regions 70''' having ring portions 73''' that house eyelets 72''' that are positioned further distally, i.e., spaced apart from proximal end of the end regions 70'''. As will be apparent, the eyelet positioning may be modified without departing from the spirit of the present embodiments. Moreover, in certain embodiments, the ring portions housing the eyelet may be disposed further proximally than shown in FIG. 12 such that the ring portions extend proximally beyond then end of the adjacent proximal apices 62b.

Referring now to FIGS. 14-15, an alternative apparatus 120 is shown for deploying a plurality of stent portions using a plurality of coiled members. The apparatus 120 is similar to the apparatus 20 of FIGS. 1-2 and FIGS. 4-5, with main exceptions noted below. In particular, the apparatus 120 of FIGS. 14-15 comprises a first coiled member 140 and a second coiled member 180, which are coupled to an outer surface 131 of a cannula 130 at locations that are longitudinally spaced apart from one another.

The first coiled member 140 comprises a proximal end 141, a distal end 142, and a plurality of turns 143 disposed therebetween. In this embodiment, the distal end 142 of the first coiled member 140 is secured to the outer surface 131 of the cannula 130 using a suitable mechanism, such as a solder, weld, mechanical attachment, friction fit, crimp, or combination of these or other techniques and mechanisms, as generally described above. The proximal end 141 of the first coiled member 140 is unsecured relative to the outer surface 131 of the cannula 130 at a location just proximal to an atraumatic tip 135, as shown in FIG. 14. The proximal end 141 of the first coiled member 140 preferably comprises the second diameter $d_2$, shown in FIG. 2 above, and provides the same separation or gap 44 described in FIG. 2 above between the proximal end 141 of the first coiled member 140 and the outer surface 131 of the cannula 130.

Similarly, the second coiled member 180 comprises a proximal end 181, a distal end 182, and a plurality of turns 183 disposed therebetween. The distal end 182 of the second coiled member 180 is secured to the outer surface 131 of the cannula 130, as generally described above, at a location distally spaced apart from the first coiled member 140, as shown in FIGS. 14-15. The proximal end 181 of the second coiled member 180 is unsecured relative to the outer surface 131 of the cannula 130, as shown in FIG. 14. The proximal end 181 of the second coiled member 180 preferably comprises the second diameter $d_2$ and provides the same separation or gap 44 between the proximal end 181 of the second coiled member 180 and the outer surface 131 of the cannula 130.

During delivery, the first coiled member 140 is coupled to a first portion of the stent-graft 50', while the second coiled member 180 is coupled to a second portion of the stent-graft 50'. In this example, the first coiled member 140 is coupled to the suture loops 65 that are coupled to the proximal apices 62a of the stent 60, as explained in FIGS. 3-5 above, while the second coiled member 180 is coupled to a central region of the graft material 90. In particular, at least one inner stent 195 is coupled to an inner surface of the graft material 90 and configured to engage the coiled member 180, in the manner generally described above with respect to FIGS. 1-5. It should be noted that while the second coiled member 180 and a portion of the cannula 130 is disposed within the graft material 90 in FIG. 15, for illustrative purposes these components are shown in solid, not dashed, lines. Advantageously, the first and second coiled members 140 and 180 may radially restrain different, spaced-apart sections of the stent-graft 50' during deployment.

Moreover, in the example of FIGS. 14-15, the first coiled member 140 has a greater number of proximal turns 143a that are spaced apart further relative to distal turns 143b to accommodate a portion of the stent-graft 50', relative to the number of proximal turns 183a that are spaced apart further relative to distal turns 183b on the second coiled member 180. Accordingly, by varying the number of proximally spaced-apart turns 143a and 183a on the first and second coiled members 140 and 180, respectively, one portion of the stent-graft 50' may be disengaged from its respective coiled member 140 or 180 before the other portion of the stent-graft 50'. In this example of FIGS. 14-15, since the second coiled member 180 has fewer proximal turns 183a that are spaced apart to accommodate the stent 195, then the stent 195 will disengage from the proximal turns 183a relatively fast to deploy the central portion of the stent-graft 50' shortly after the cannula 130 is rotated. Subsequently, as the cannula 130 is rotated further, the suture loops 65 coupled to the proximal apices 62a of the stent 60 will disengage from the greater number of proximal turns 143a of the first coiled member 140 to deploy the proximal stent 60, after the central portion of the stent-graft 50 has been deployed.

As will be appreciated, any number of coiled members may be provided along the length of the cannula to selectively control deployment of any number of corresponding regions along a stent or stent-graft. By varying the number of spaced-apart turns, different portions of the stent or stent-graft may be selectively deployed before other portions simply by continuing to rotate a single cannula comprising the multiple coiled members.

Moreover, the portions of the stent-graft 50' that are coupled to the first and second coiled members 140 and 180 may be at least partially opened and closed to allow for a degree of repositioning before final deployment. For example, rotating the cannula 130 in a first direction may cause the portions of the stent-graft 50' to expand at least partially radially outward, while rotation in the opposing direction may cause the portions of the stent-graft 50' to contract radially inward, and this may be repeated any number of times before final deployment.

If the coiled members are unsecured relative to the cannula at their proximal ends, as depicted in FIGS. 14-15, then the cannula may be rotated in the opposite direction to achieve deployment, as compared to the coiled member 40 of FIGS. 1-2 that is unsecured at its distal end. In any of the embodiments herein, the cannula may comprise one or more coiled members that are unsecured at their proximal ends or unsecured at their distal ends, or combinations thereof in which at least one coiled member is unsecured proximally and at least one coiled member is unsecured distally.

Figure 16:
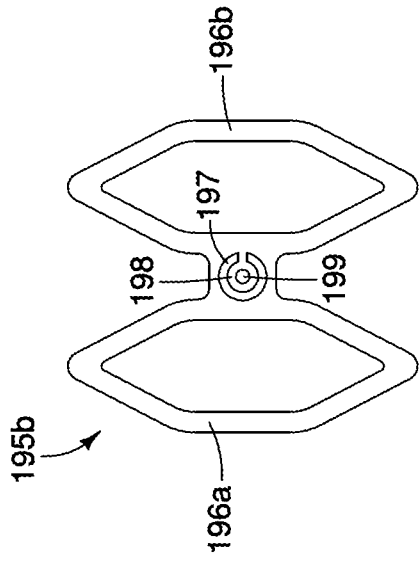
FIG. 16 is a side view of a portion of a stent suitable for use as an inner stent of the stent-graft of FIG. 15.
Figure 17:
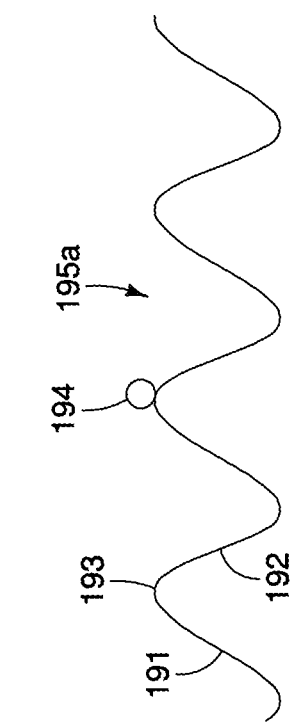
FIG. 17 is a side view of a portion of an alternative stent suitable for use as an inner stent of the stent-graft of FIG. 15.

Referring to FIGS. 16-17, examples of stents that are suitable for use as the inner stent 195 of FIG. 15, which may be coupled to the second coiled member 180, are shown and described. In FIG. 16, a stent 195a comprise a zig-zag shape comprising first and second generally straight segments 191 and 192 that are angled relative to one another and separated by a plurality of apices 193. An eyelet 194 may be coupled to one of the apices 193, as shown in FIG. 16, or any other suitable segment of the stent 195a. In use, the unsecured, spaced-apart proximal turns 183a of the second coiled member 180 are disposed through the eyelet 194 of the stent 195a, thereby securing the stent 195a to the second coiled member 180.

In FIG. 17, a stent 195b comprises a cannula-cut structure having first and second cells 196a and 196b, which are separated by a spacing. A partial circumferential slit 197 is formed in the spacing to create a ring member 198, and a bore 199 then is formed within the ring member 198, as depicted in FIG. 17. The ring member 198 having the bore 199 then may be bent radially inward at a desired angle, such as between 45 and 90 degrees, and then heat-set into the bent position, as generally described with respect to the ring member 73" and 73''' of FIGS. 12-13, to facilitate engagement with the second coiled member 180.

Figure 18:
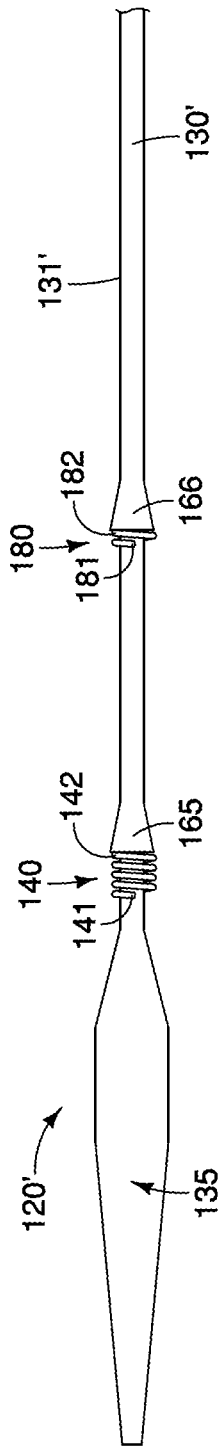
FIG. 18 is a side view of a further alternative embodiment of an apparatus for deploying stent portions using first and second coiled members.

Referring to FIG. 18, an alternative apparatus 120' is shown for deploying a plurality of stent portions using a plurality of coiled members, and is similar to the apparatus 120 of FIGS. 14-15, with main exceptions noted below. In particular, an alternative cannula 130' of the apparatus 120' comprises a plurality of tapers 165 and 166 that increase in diameter from distal to proximal directions. The largest diameters of the tapers 165 and 166 generally match the second diameters $d_2$, explained above in FIG. 2, of the first and second coiled members 140 and 180, respectively.

Accordingly, the proximal ends of the tapers 165 and 166 are substantially flush with the outer diameters $d_2$ of the first and second coiled members 140 and 180. In this embodiment, the distal ends 142 and 182 of the first and second coiled members 140 and 180 may be secured to the proximal ends of the tapers 165 and 166, respectively, e.g., using a solder or other suitable technique, thereby eliminating the provision of the smaller turns of the first and second coiled members 140 and 180.

Referring now to FIGS. 19-20, a further alternative apparatus 220 is shown for deploying a portion of a stent 260 using a coiled member 240. In FIGS. 19-20, a cannula 230, which is similar to the cannula 30 described above, comprises an outer surface 231, an atraumatic tip 235, and a wire guide lumen 239. The coiled member 240 comprises proximal and distal ends 241 and 242, respectively, and a plurality of turns 243 disposed therebetween. The distal end 242 of the coiled member 240 is secured to the outer surface 231 of the cannula 230, e.g., using solder or weld 249, while the proximal end 241 of the coiled member 240 is unsecured relative to the outer surface 231 of the cannula 230, as depicted in FIGS. 19-20.

The apparatus 220 further comprises a swivel 270 coupled to the cannula 230 at a location proximal to the coiled member 240, and a plurality of suture loops 275a and 275b. Each of the suture loops 275a and 275b comprises a proximal region 276 that is coupled to the swivel 270, e.g., by being disposed through a bore 271 in the swivel 270, and further comprises a distal region 277 that is retained in a delivery state beneath one of the plurality of turns 243 of the coiled member 240, as depicted in FIGS. 19-20. The stent 260 comprises a first proximal apex 262a that is coupled to the suture loop 275a, and further comprises a second proximal apex 262b that is coupled to the suture loop 275b. The suture loops 275a and 275 are disposed around portions of the first and second proximal apices 262a and 262b, respectively, in a manner that restrains the first and second proximal apices 262a and 262b in the delivery state of FIG. 19.

The first and second proximal apices 262a and 262b of the stent 260 are movable between a first configuration of FIG. 19 in which they are restrained radially inward, a second configuration of FIG. 20 in which they are at least partially deployed radially outward, and a final configuration in which they are fully deployed. In the first configuration of FIG. 19, the distal regions 277 of the suture loops 275a and 275b are positioned beneath the plurality of turns 243 at a location distally away from the swivel 270, thereby maintaining the suture loops 275a and 275b in a state of relative tension in which the suture loops 275a and 275b are generally parallel to the cannula 230, which holds the first and second proximal apices 262a and 262b in a radially restrained state. In the second configuration of FIG. 20, the cannula 230 may be rotated in a direction that causes the distal regions 277 of the suture loops 275a and 275b to move closer to the swivel 270, thereby providing slack for the suture loops 275a and 275b and allowing the first and second proximal apices 262a and 262b to be at least partially deployed radially outward based on their resilient nature.

Advantageously, if a physician does not wish to ultimately deploy the first and second proximal apices 262a and 262b when in the partially deployed state of FIG. 20, the physician may then rotate the cannula 230 in an opposing direction that causes the suture loops 275a and 275b to resume a state of relative tension to move the first and second proximal apices 262a and 262b radially inward to the state of FIG. 19, thereby allowing for repositioning of the first and second proximal apices 262a any number of times after partial deployment. Therefore, the embodiment of FIGS. 19-20 provides a degree of reversibility prior to final deployment. Ultimately, a physician can deploy the first and second proximal apices 262a and 262b at the desired location by rotating the cannula 230 to cause the distal regions 277 of the suture loops 275a and 275b to pass proximally beyond the proximal end 241 of the coiled member 240. The suture loops 275a and 275b are then free from engagement with the first and second proximal apices 262a and 262b, and the cannula 230 may be removed from the patient's body with the suture loops 275a and 275b still coupled to the swivel 270.

Optionally, if circumferential orientation of the stent 260 is important, then to permit better circumferential positioning at the proximal end of the stent 260, a single trigger wire or other means may be used to temporarily lock the swivel 270 in place circumferentially as the stent 260 is positioned within the body. In this example, the single trigger wire or other means can be disengaged from the swivel 270, e.g., by being withdrawn from one of the bores 271 of the swivel 270, upon proper orientation within the body when the stent 260 is still in the delivery state, to thereby permit subsequent rotation of the swivel 270 and allowing unwinding of the suture loops 275a and 275b from the coiled member 240 as the cannula 230 is rotated.

Referring now to FIGS. 21-24, an apparatus 320 is shown for deploying a portion of a stent 360 using at least one coiled member 140, and comprises a protective cage 370 for enclosing the coiled member 140. In this example, the exemplary coiled member 140 is the same coiled member that is secured to the outer surface 131 of the cannula 130, as explained above in FIG. 14, though it is contemplated that the protective cage 370 may be used in conjunction with other coiled members, including those alternative coiled members shown herein.

Figure 21:
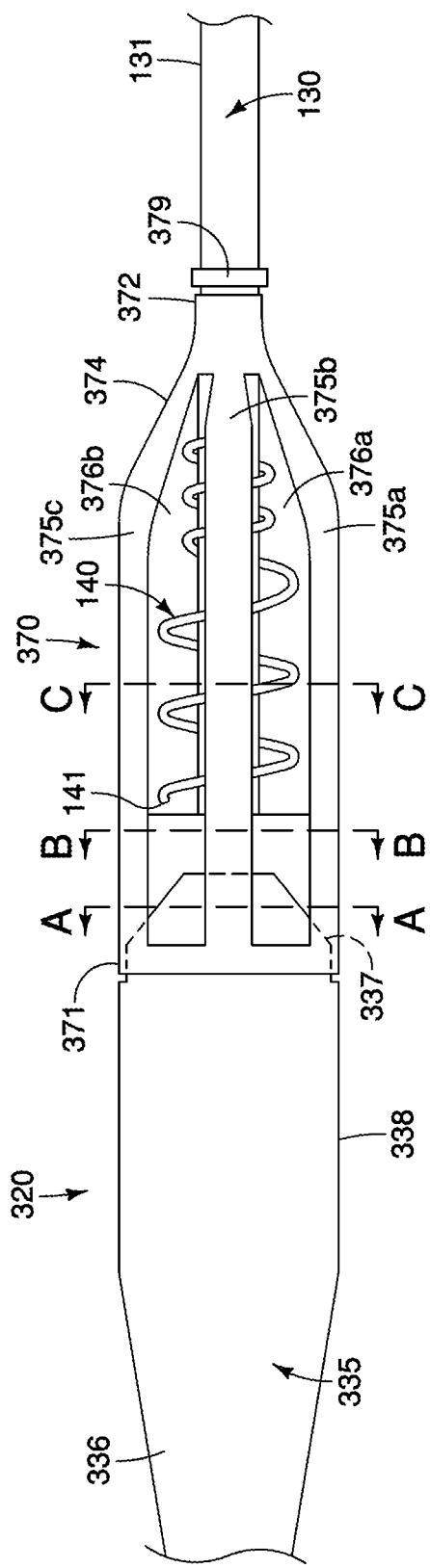
FIG. 21 is a side view of an embodiment of a protective cage that may be used in conjunction with the coiled member.

The protective cage 370 comprises a first end 371 having an outer diameter $dc_1$, and a second end 372 having a second outer diameter $dc_2$, as best seen in FIGS. 21 and 24. In the embodiment of FIGS. 21-24, where the exemplary coiled member 140 is secured to the cannula 130 at its distal end and unsecured at its proximal end, then the first end 371 having the first outer diameter $dc_1$ will be the proximal end of the protective cage 370, while the second end 372 having the second outer diameter $dc_2$ will be the distal end of the protective cage 370. It is noted that the diameter at the first or proximal end 371 of the protective cage 370 can be larger to accommodate the greater diameter of the coil at its unsecured proximal end that is spaced apart relative to the cannula 130, as depicted by separation or gap 44 in FIG. 2 above. At the second or distal end 372 of the protective cage 370, the reduced second outer diameter $dc_2$ may be provided because the diameter of the coiled member 140 is reduced for coupling to the cannula 130. Further, the second or distal end 372 of the protective cage 370 may be positioned distally of the coiled member 140, as shown in FIG. 21, and the second outer diameter $dc_2$ may be slightly larger than the outer surface 131 of the cannula 130. It should be noted that a taper 374 reduces the diameter of the protective cage 370 between the first end having the outer diameter $dc_1$ and the second end having the reduced outer diameter $dc_2$.

It should be noted that, if the unsecured end of the coiled member is located distally instead of proximally, then the axial orientation of the protective cage 370 may be reversed. For example, if the coiled member 40 of FIGS. 1-2 and 4-5 is used, which is unsecured at its distal end, then the protective cage 370 may have the first end 371 of greater diameter located distally, while the second end 372 of lesser diameter is located proximally, thereby generally corresponding to the shape of the coiled member.

Figure 22:
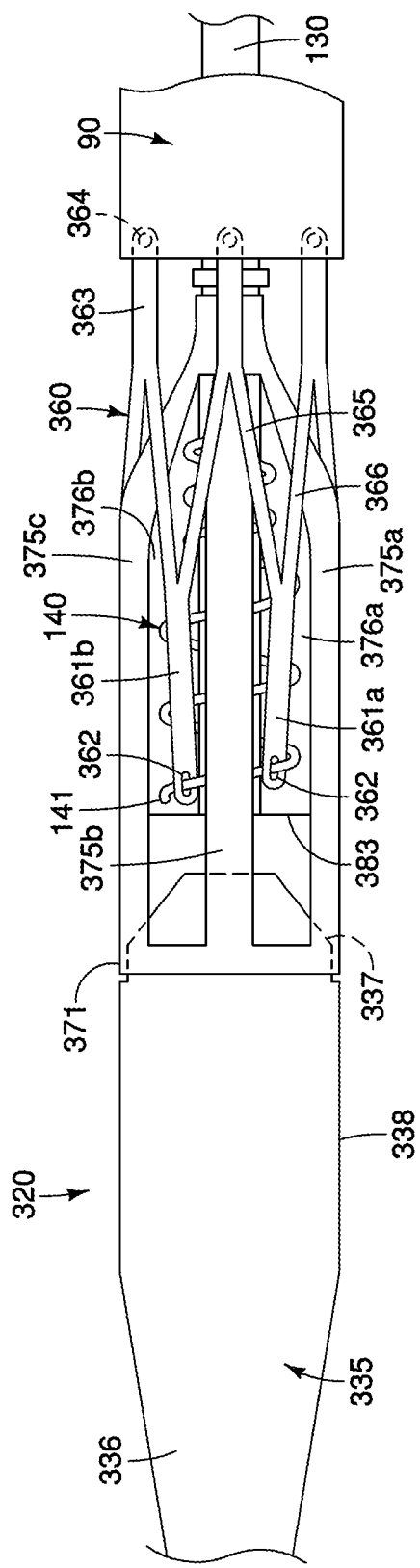
FIG. 22 is a side view depicting a portion of a stent used with the apparatus of FIG. 21.

In the embodiment of FIGS. 21-24, the protective cage 370 further comprises a plurality of struts 375 separated by a plurality of slots 376. In this non-limiting example, four struts 375a-375d are depicted as being separated by four slots 376a-376d, as depicted among the various FIGS. 21-22, 23A-23C and 24. However, any number of slots and struts may be provided. Moreover, the number of slots may correspond directly to the number of proximal apices 361 of the stent 360 that need to be restrained, as generally depicted in FIG. 22 and explained below, or there may be variability between the number of slots and the number of proximal apices of the stent 360.

Each of the struts 375a-375d and slots 376a-376d have proximal and distal ends, and are generally parallel to each other in a direction running along a longitudinal axis of the apparatus, as shown in FIG. 21. Each of the slots 376a-376d has a width that is greater than a width of the proximal apices 361 of the stent 360, thereby allowing portion of the proximal apices 361 to extend through an associated slot, as depicted in FIG. 22. Each of the slots 376a-376d may accommodate one proximal apex 361, or multiple proximal apices.

In one embodiment, the protective cage 370 is designed to cooperate with at least a portion of an atraumatic tip 335. In FIGS. 21-24, the atraumatic tip 335 may comprise proximal and distal regions 336 and 337, respectively, and a central region 338 disposed therebetween. The proximal and distal regions 336 and 337 comprise a smaller outer diameter relative to the central region 338, with a first taper allowing for a smooth transition between the proximal region 336 and the central region 338, and a second taper allowing for a smooth transition between the distal region 337 and the central region 338. The proximal region 336 may comprise a similar shape to the proximal region 36 of the atraumatic tip 35 of FIG. 1 and FIGS. 4-5.

The distal region 337 of the atraumatic tip 335 may comprise an outer surface that corresponds to the shape of an inner surface at a proximal region of the protective cage 370. In particular, the protective cage 370 comprises a proximal inner taper 381, as shown in FIG. 24. The outer surface of the distal region 337 of the atraumatic tip 335 generally annularly abuts the proximal inner taper 381 in an assembled state.

In accordance with one aspect, the protective cage 370 can rotate circumferentially relative to the atraumatic tip 335 and the cannula 130. Notably, the proximal inner taper 381 of the protective cage 370 is disposed around the distal region 337 of the atraumatic tip 335, while the distal end 372 of the protective cage 370 is disposed around the outer surface 131 of the cannula 130. Since the proximal and distal regions of the protective cage 370 are not secured to the atraumatic tip 335 and the cannula 130, respectively, the protective cage 370 can rotate circumferentially relative to these adjacent components.

A distal stop member 379 may be positioned adjacent to the distal end 372 of the protective cage 370, as shown in FIG. 21. The distal stop member 379 allows the protective cage 370 to rotate relative to the cannula 130, but prevents the protective cage 370 from sliding distally over the cannula 130. The distal stop member 379 may be formed integrally with the cannula 130, or as an external component secured to the outer surface 131 of the cannula, and may comprise any suitable biocompatible material.

The proximal inner taper 381 of the protective cage 370 extends inward to an opening 382, shown in FIG. 24, which has a diameter that allows passage of the cannula 130 so that the cannula 130 can be coupled to the atraumatic tip 335. Moreover, a stepped surface 383 is provided just distal to the opening 382, as shown in FIG. 24. The stepped surface 383 may be generally perpendicular to the longitudinal axis of the cannula 130. The stepped surface 383 prevents the proximal apices 361 of the stent 360 from sliding off of the coiled member 140 prematurely, and may reduce the possibility that the proximal apices 361 of the stent 360 become inadvertently lodged under the struts 375a-375d. Preferably, the proximal end 141 of the coiled member 140 is disposed immediately adjacent to the stepped surface 383, as depicted in FIG. 21, thereby further reducing the possibility of inadvertent uncoupling of the proximal apices 361 of the stent 360 from the coiled member 140 prior to desired rotation of the cannula 130.

The protective cage 370 further comprises a main housing 384, which is disposed between the stepped surface 383 and the distal end 372, as shown in FIG. 24. The main housing 384 is sized for housing the coiled member 140 therein, and has an inner diameter that remains larger than the coiled member along its longitudinal length, thereby permitting rotation of the coiled member 140 within the main housing 384.

The protective cage 370 may be formed from stainless steel, nitinol, polymers, or other suitable biocompatible materials. Moreover, the protective cage 370 may be manufactured as a single component, or multiple components that are secured together. In one embodiment, the protective cage 370 may be manufactured by forming an outer shell of material, and then inserting material that forms the proximal inner taper 381 and the stepped surface 383, and separately cutting the slots 376a-376d into the outer shell.

In the non-limiting example of FIG. 22, the stent 360 comprises a series of proximal apices 361 and a series of distal apices 363. Each of the proximal and distal apices 361 and 363 are separated by a plurality of strut segments 365 and 366, which enable radial expansion from the compressed state shown in FIG. 22 to a generally cylindrical expanded state similar to the stent 60 depicted in FIG. 4. The distal apices 363 may be coupled to graft material 90 using sutures threaded through one or more bores 364 formed in the distal apices 363 that overlap with the graft material, as shown in FIG. 22.

The manner of using the apparatus 320 is similar to use of the prior apparatuses 20 and 120, explained above. However, in the embodiment of FIGS. 21-24, the proximal apices 361 of the stent 360 are coupled to the coiled member through the slots 376a-376d. For example, a first proximal apex 361a may be positioned over the slot 376a, as depicted in FIG. 22, and the proximal end 141 of the coiled member 140 may be aligned with a coupling member 362 of the first proximal apex 361a. The coupling member 362 of FIG. 22 may be in the form of the suture loop 65, the wire loop 54, or any one of the eyelets 72, 72', 72", 72'" described above, or another suitable connector coupled to the proximal apex 361a, which can be coupled or looped around the proximal end 141 of the coiled member 140. The proximal apex 361a may be pushed radially inward and held steady, while the cannula 130 and the coiled member 140 are rotated in a first direction, thereby allowing the coupling member 362 of the proximal apex 361a to be wound in a proximal to distal direction securely about the coiled member 140. Subsequently, a second proximal apex 361b may be positioned over the slot 376b and the same process achieved to couple the second proximal apex 361b about the coiled member 140, and this process may be repeated until all of the proximal apices 361 of the stent 360 are coupled to the coiled member 140, through the slots 376a-376d, as shown in FIG. 22. As noted above, there may be a one-to-one ratio of proximal apices 361 of the stent 360 to slots in the protective cage 370, or alternatively, multiple proximal apices 361 of the stent 360 may be coupled to the coiled member 140 through the same slot in the protective cage 370.

After all of the proximal apices 361 of the stent 360 are coupled to the coiled member 140 through the slots 376a-376d of the protective member, a physician may deploy the stent 360 in the same manner as the explained in FIGS. 4-5 above. In particular, upon proper positioning at the target site using a desired imaging modality, an outer sheath is retracted to expose at least a portion of the stent 360. When the stent 360 is at least partially exposed, and it is desirable to deploy the proximal end of the stent 360, the cannula 130 may be rotated in a counter-clockwise direction until the coupling member 362 of the first proximal apex 361a is uncoupled from the coiled member 140, i.e., in a reverse manner from which these connectors were coupled to the coiled member 140. The stent 360 then may be deployed as shown in FIG. 4 above, and the remainder of the stent-graft may be deployed by further retraction of the outer sheath or actuation of any other devices that are radially constraining the remainder of the stent-graft.

Advantageously, during deployment of the stent 360 using the protective cage 370, the protective cage 370 can rotate circumferentially relative to the atraumatic tip 335 and the cannula 130. This allows the orientation of the protective cage 370 and the stent apices 361 to remain generally the same while the cannula 130 and the coiled member 140 are rotated circumferentially during deployment.

As a further advantage, the protective cage 370 encloses the coiled member 140 and reduces the possibility that the coiled member 140 can interfere with, damage, or snag various endovascular, stent or graft structures during manipulation and removal of the delivery device. The protective cage 370 also may reduce the likelihood of apices of the stent 360 becoming caught on the coiled member 140 by providing a guided release for the apices.

As noted above, if the unsecured end of the coiled member is located distally instead of proximally, then the axial orientation of the protective cage 370 may be reversed. Moreover, if multiple coiled members are used, e.g., as in the embodiment of FIGS. 14-15, then multiple protective cages 370 may be provided that each enclose a different coiled member.

Figure 25:
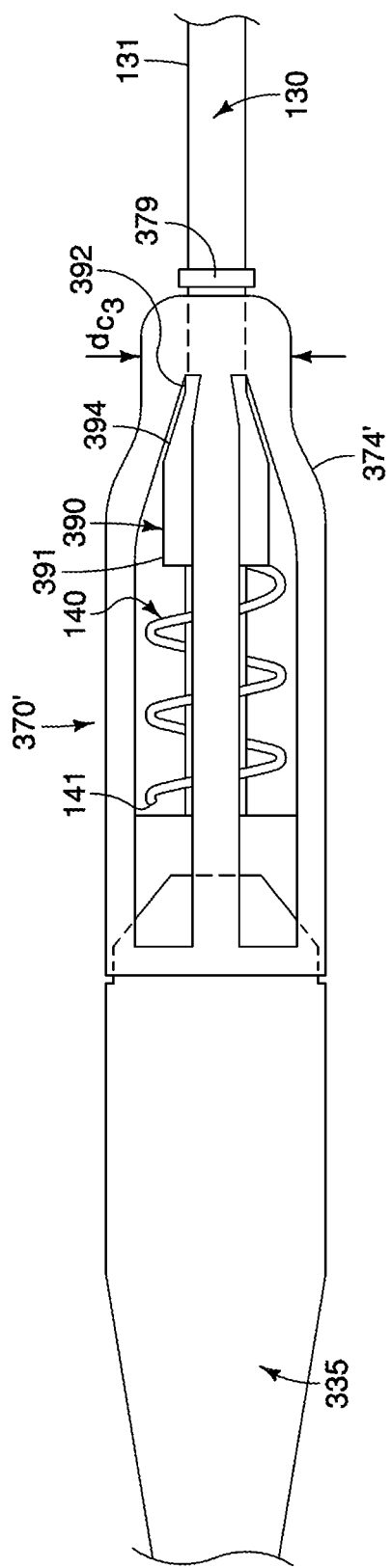
FIG. 25 is a side view of an alternative protective cage.

Referring now to FIG. 25, an alternative protective cage 370' is similar to the protective cage 370 of FIGS. 21-24, with like reference numbers representing like parts, except as noted below. In this example, an enclosing member 390 that surrounds the distal end 142 of the coiled member 140 that is secured to the outer surface 131 of the cannula 130. The enclosing member 390 may comprise a first end 391 that is spaced apart from the cannula 130 to accommodate a portion of the coiled member 140, a second end 392 that is secured to the outer surface 131 of the cannula 130, and a tapered region 394 that bridges the different diameters of the first and second ends 391 and 392, as depicted in FIG. 25. The alternative protective cage 370' may comprise a longitudinal region 374', as shown in FIG. 25, which comprises an intermediate outer diameter $dc_3$, which has a dimension less than the first end 371 having the outer diameter $dc_1$ and greater than the second end 372 having the outer diameter $dc_2$, as depicted in the earlier embodiment of FIG. 24. The longitudinal region 374' further has an inner diameter that is slightly larger than an outer diameter at the first end 391 of the enclosing member 390. Advantageously, the enclosing member 390 provides a barrier between a portion of the coiled member 140 and the protective cage 370', which may reduce potential drawbacks arising from direct interference between the distal end 142 of the coiled member 140 and the protective cage 370'.

Figure 26:
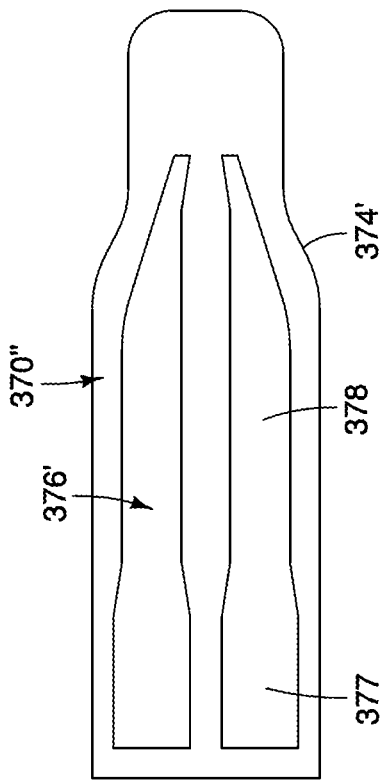
FIG. 26 is a side view of a further alternative protective cage.

Referring now to FIG. 26, an alternative protective cage 370" is similar to the protective cages 370 and 370' above, with a main exception that a plurality of slots 376' has proximal regions 377 that are wider than distal regions 378. The widening of proximal regions 377 of the slots 376' may yield an easier time coupling the stent 360 to the coiled member 140 during loading, and may facilitate release of the stent 360 from the coiled member 140 given less potential interference from the proximal region 377 of the slots 376'. The proximal apices 361 of the stent 360 can also be modified, e.g., with widened proximal tips, so that they only side out of the protective cage 370" at the proximal region 377 of the slots 376'.

Figure 28:
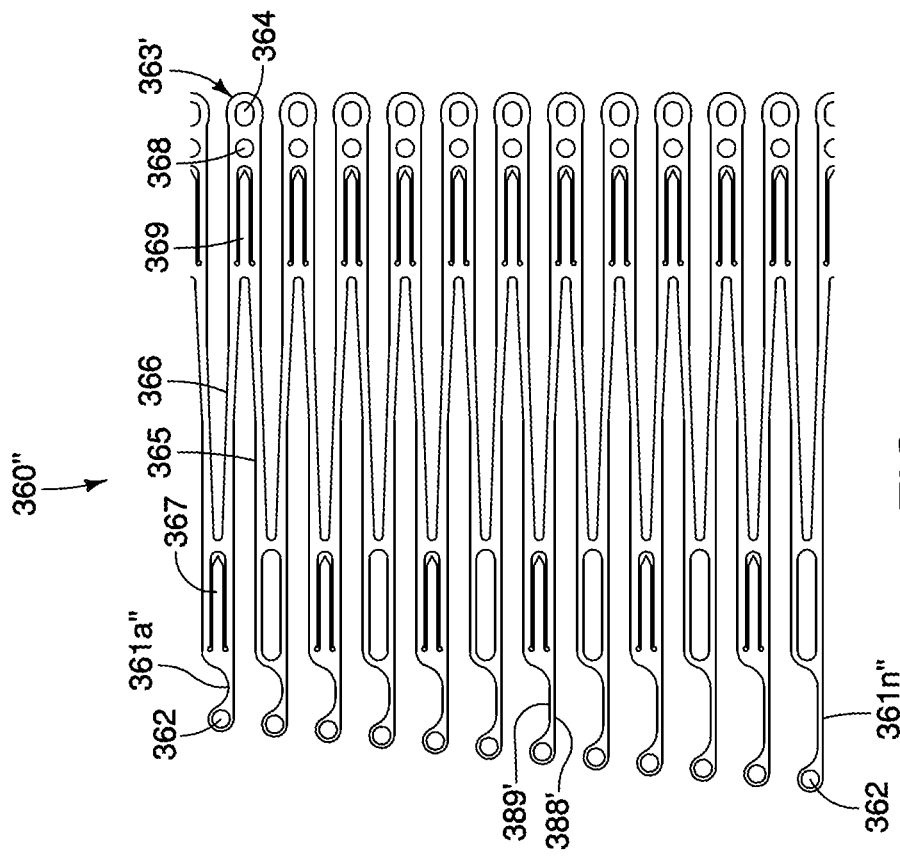
FIG. 28 is a side view of an alternative stent, shown in a flattened and compressed state, which is suitable for deployment using a coiled member.
Figure 27:
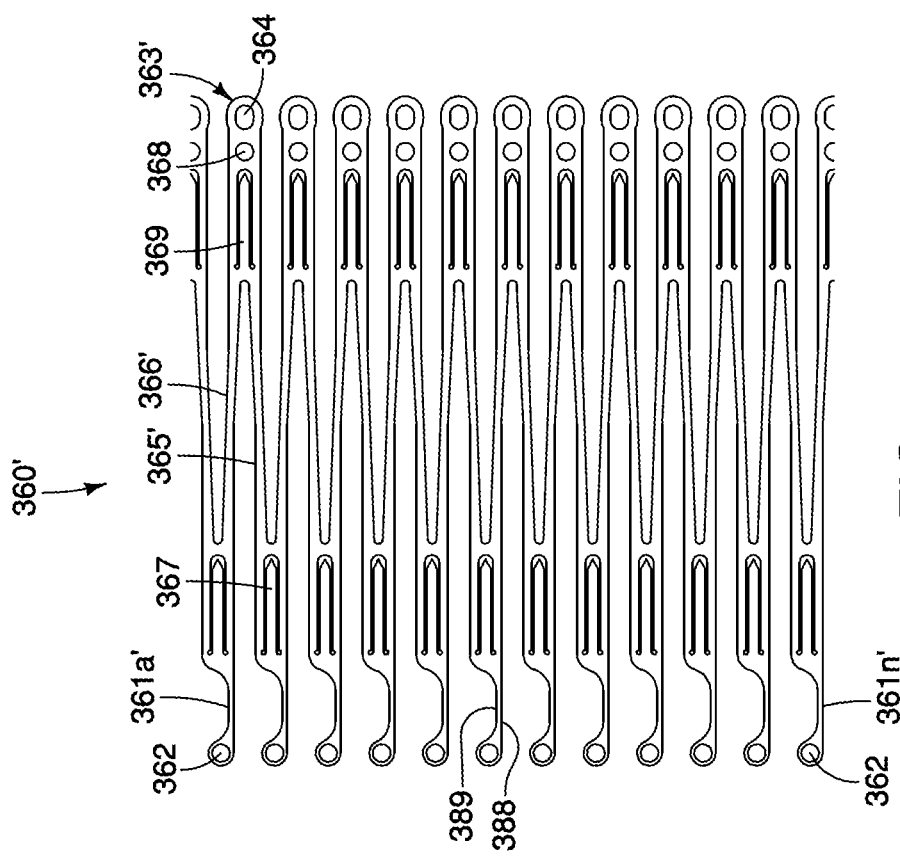
FIG. 27 is a side view of a stent, shown in a flattened and compressed state, which is suitable for deployment using a coiled member.

Referring now to FIGS. 27-28, two different stent designs are shown, which are alternatives to the stents 60 and 360 described above. In FIG. 27, a stent 360', which is shown in a flattened and compressed state, comprises a series of proximal apices 361' and a series of distal apices 363'. Each of the proximal and distal apices 361' and 363' are separated by a plurality of strut segments 365' and 366', which enable radial expansion from the compressed state shown in FIG. 27 to a generally cylindrical expanded state similar to the stent 60 depicted in FIG. 4.

Each of the proximal apices 361' comprises the coupling member 362, as explained with respect to FIG. 22 above, and further comprises an integral barb 367. Each of the distal apices 363' comprises a suture bore 364', an imaging marker 368, and an integral barb 369. The suture bore 364' overlaps with graft material 90, as depicted in FIG. 22, and allows suturing of a portion of each distal apex 363' to the graft material 90. The imaging marker 368, which is disposed proximal to the suture bore 364', may be aligned precisely with the proximal edge of the graft material 90 to enable precise placement of the proximal edge under an imaging modality.

The stent 360' may comprise any number 361n' of proximal apices 361', where "n" is the number of apices. In the example of FIG. 27, "n" is equal to twelve, and each of the twelve proximal apices 361a' through 361n' have identical characteristics, including axial lengths. A first proximal apex 361a' is loaded onto the coiled member 40 or 140 in the manner described above via engagement with the coupling member 362, and each subsequent proximal apex 361 is secured to the coiled member 40 or 140 until the final proximal apex 361n' is secured to the coiled member. It should be noted that each of the proximal apices 361a' through 361n' comprises a region having a relatively thin strut segment 388, having a notched region 389 formed therein, which advantageously may permit this region of the proximal apex to rotate or bend to facilitate coupling to the coiled member 40 or 140, in the manner described above for the proximal extension segment 74 of FIGS. 6-8.

Referring now to FIG. 28, an alternative stent 360" is identical to the stent 360' of FIG. 27, with the exception that alternative proximal apices 361" comprise different axial lengths relative to one another. In the example of FIG. 28, each of the alternative proximal apices 361" comprises a progressively larger axial length, such that a first proximal apex 361a" comprises the smallest axial length, while the last proximal apex 361n" comprises the greatest axial length. Axial lengths of relatively thin strut segments 388' and their associated notched regions 389' may be varied to achieve the length differential between adjacent proximal apices 361a" through 361n", which yields a staggered axial positioning of the coupling members 362 of each apex, as shown in FIG. 28. The first proximal apex 361a" is loaded onto the coiled member 40 or 140 in the manner described above via engagement with the coupling member 362, and each subsequent proximal apex 361 is secured to the coiled member 40 or 140 until the final proximal apex 361n" is secured to the coiled member.

The axial length differential between coupling members 362 of adjacent proximal apices 361a" through 361n" can be determined according to the formula $i=p/n$, where "i" is the axial length between coupling members 362 of adjacent proximal apices 361a" through 361n", "p" is the pitch of the coiled member, and "n" is the number of proximal apices. For example, where there are twelve proximal apices 361a" through 361n", the value of "i" may equal 0.167 mm where the pitch of the coiled member is 2.0 mm, i.e., $i=p/n$ corresponds to 0.167 mm=2.0 mm/12.

Advantageously, by modifying the axial length between adjacent proximal apices 361a" through 361n", and yielding the staggered axial positioning of the coupling members 362 of each apex, capture of the coupling members 362 may be facilitated during securement to the coiled members 40 and 140. Further, the coupling members 362 can endure lower strains since the first proximal apex 361a" does not have to bend more to accommodate other points during the loading process. The proximal apices 361a" through 361n" can therefore be positioned in a uniform radially about the coiled member 40 or 140.

Referring now to FIG. 29, an alternative atraumatic tip 435 comprises proximal and distal regions 436 and 437, respectively, and a central region 438 disposed therebetween. The proximal and distal regions 436 and 437 comprise smaller outer diameters relative to the central region 438, with a first taper allowing for a smooth transition between the proximal region 436 and the central region 438, and a second taper allowing for a smooth transition between the distal region 437 and the central region 438. In this example, a distal taper 439 is formed at an angle α relative to the central region 438 and also to the main longitudinal axis of the device. The angle α preferably is minimized to achieve a minimal distance for threading the coupling members 362 of the stents on and off the coiled members 40 and 140. Additionally, in this example, a length of a distal face 449 of the atraumatic tip 439 may be greater than the second outer diameter $d_2$ of the coiled member 140, as illustrated previously. By having the second outer diameter $d_2$ of the coiled member 140 be less than the length of the distal face 449 of the atraumatic tip 439, the chances of inadvertent snagging of the proximal end 141 of the coiled member 140 may be reduced.

Further, a distance x between the proximal end 141 of the coiled member 140 and the distal end of the atraumatic tip 435 may be optimized so that the distance x is just slightly larger than an axial length necessary for coupling the coupling members 362 of the stents on and off the coiled members 40 and 140. By minimizing the distance x, the likelihood of the coupling members 362 of the stents becoming inadvertently disengaged from the coiled members 40 and 140 is reduced. Further, by minimizing the distance x, the likelihood of the coiled member 140 snagging on another part of the delivery system or a bodily structure may be reduced.

Figure 31:
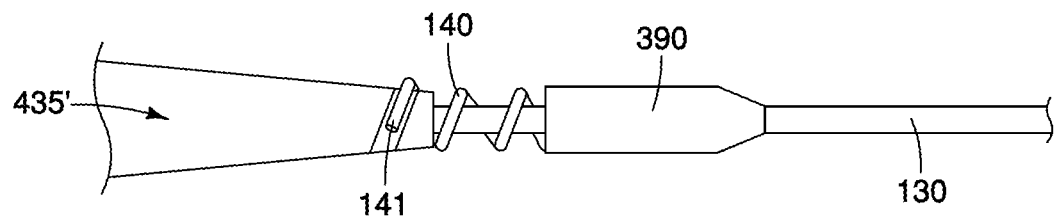
FIGS. 31-32 are, respectively, images depicting first and second states of the coiled member of FIG. 30.
Figure 32:
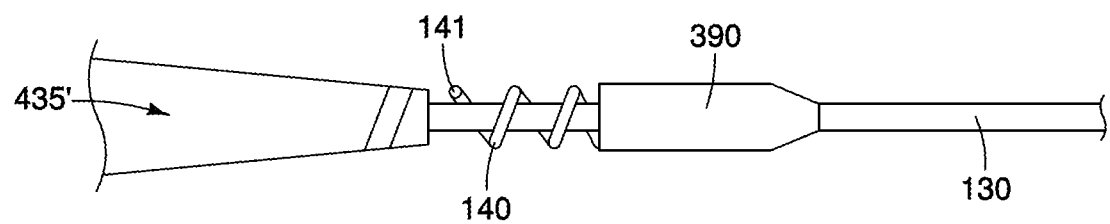

Referring now to FIGS. 30-32, an alternative atraumatic tip 435' is similar to the atraumatic tip 435 of FIG. 29, but comprises an alternative distal region 437' having a notched region 440 formed in the distal face of the atraumatic tip 435'. The notched region 440 generally follows at least a portion of the profile of the coiled member 140, as shown in FIG. 30. Further, the distance x between the proximal end 141 of the coiled member and the distal end of the atraumatic tip 435, as explained in FIG. 29, may be maintained in the embodiment of FIGS. 30-32, although in an angled manner that corresponds to the angular profile of the coiled member 140, as best seen in FIG. 30.

In this example, the notched region 440 follows the contours of a longitudinal notch 441 and angled segments 442 and 443, which collectively allow for the separation distance x between the coiled member 140 and the atraumatic tip 435' to be maintained while the proximal end 141 of the coiled member 140 at least partially axially overlaps with the atraumatic tip 435'. A first state of the delivery system is shown in FIGS. 30 and 31, in which the proximal end 141 of the coiled member 140 at least partially axially overlaps with the atraumatic tip 435', may be used during delivery into, and removal from, a patient's vascular system. A second state of the delivery system is shown in FIG. 32, in which the proximal end 141 of the coiled member 140 has been rotated to be disposed distal to the atraumatic tip, may occur during deployment as the stent-graft is held longitudinally steady. In one further embodiment, the atraumatic tip 435' may be longitudinally movable relative to the coiled member 140, such that when deployment of the stent-graft is completed, the atraumatic tip 435' may be advanced distally relative to the coiled member 140 until the proximal end 141 of the coiled member is at least partially seated within the notched region 440 of the atraumatic tip 435' for subsequent removal from the vasculature.

In the embodiment of FIGS. 30-32, multiple advantages are achieved. First, the likelihood of the coupling members 362 of the stents becoming inadvertently disengaged from the coiled member 140 is reduced. Further, since the proximal end 141 of the coiled member 140 at least partially axially overlaps with the atraumatic tip 435', the likelihood of the coiled member 140 snagging on another part of the delivery system or a bodily structure may be significantly reduced.

Referring now to FIGS. 33-35, a further alternative atraumatic tip 435" is similar to the atraumatic tips 435 and 435' of FIGS. 29-32, but comprises an alternative distal region 437" having a notched region 440", and an alternative central region 438" having a channel 450. It is noted that the coiled member 140 is omitted in FIG. 33 for clarity, but is shown in FIG. 35.

The notched region 440" may comprise tapered wall portions 441 and 442, which taper in an angled manner radially inward to a valley 443. The valley 443 has proximal and distal ends 443a and 443b, respectively, as depicted in FIG. 35. The proximal end 443a of the valley 443 may transition into the channel 450 of the central region 438" of the atraumatic tip 435". The channel 450 may be used as a conduit for delivering flushing fluid, which may be provided in a distal to proximal direction through the valley 443 and subsequently through the channel 450.

The distal end 443b of the valley 443 is disposed in close longitudinal proximity, and preferably slightly proximal to, the proximal end 141 of the coiled member 140. The distance between the proximal end 141 of the coiled member 140 and the distal end of the atraumatic tip 435" remains such that there is sufficient space for the coupling members 362 of stents to be released from the coiled member 140, as described above. Further, the proximal end 141 of the coiled member 140 may terminate at a circumferential location slightly offset from the center of the valley 443. For example, in FIG. 35, the proximal end 141 of the coiled member 140 is shown slightly above the center of the valley 443, and about even with the tapered wall portion 441. In this manner, the center of the valley 443 will be aligned precisely with the coupling members 362 as they exit from engagement with the proximal end 141 of the coiled member 140.

In the embodiment of FIGS. 33-35, multiple advantages are achieved. As one example, the valley 443 may significantly reduce the likelihood of the atraumatic tip 435" becoming caught on a radially deployed coupling member 362. In particular, after deployment of the stent, the delivery system including the atraumatic tip 435" will be retracted distally outside of the patient, and during the phase of initial retraction, the valley 443 helps provide a ramp-like feature to ensure that the deployed coupling member 362 of the stents will not become caught on the atraumatic tip 435" upon its removal.

The valley 443 of the notched region 440" also provides a ramp-like pathway for the coupling members 362 to follow as they move radially outward from the proximal end 141 of the coiled member 140 towards a vessel wall. Accordingly, the provision of the valley 443 may significantly reduce the likelihood of the coupling members 362 of the stents becoming caught on the atraumatic tip 435" during deployment, in addition to after deployment.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A system for deploying at least a portion of a stent, the system comprising:
    a delivery device; and
    a stent that is releasably secured to a portion of the delivery device,
    where the stent comprises a main body region having a plurality of proximal and distal apices;
    a coupling member extending axially away from at least one of the plurality of proximal and distal apices, wherein the coupling member is releasably secured to the delivery device,
    where the coupling member comprises a ring portion having an eyelet, and an extension segment positioned axially between the ring portion and the at least one of the plurality of proximal and distal apices,
    where the eyelet encircles a section of the delivery device in a delivery state,
    where the extension segment comprises a wall thickness that is less than a wall thickness of other regions of the stent to facilitate twisting of the ring portion in a first direction relative to the main body region.

2. The system of claim 1, where the ring portion is set into a bent position relative to the main body region.

3. The system of claim 1, where the ring portion twists at least 30 degrees relative to the main body region to facilitate coupling of the stent to the delivery device.

4. The system of claim 3, where the ring portion twists about 90 degrees relative to the main body region to facilitate coupling of the stent to the delivery device.

5. The system of claim 3, where the ring portion twists greater than 90 degrees relative to the main body region to facilitate coupling of the stent to the delivery device.

6. The system of claim 1, where the at least one of the plurality of proximal and distal apices comprises an integral barb, where the coupling member extends in a direction axially away from the integral barb.

7. The system of claim 1, where the ring portion and the extension segment are integrally formed with the at least one of the plurality of proximal and distal apices.

8. The system of claim 1, where the delivery device comprises a cannula having an outer surface, and a coiled member having proximal and distal ends, where at least a portion of the coiled member is secured to the outer surface of the cannula,
where the coupling member is releasably secured to a portion of the coiled member.

9. A system for deploying at least a portion of a stent, the system comprising:
a delivery device; and
a stent that is releasably secured to a portion of the delivery device,
where the stent comprises a main body region having a plurality of proximal and distal apices;
a coupling member extending axially away from at least one of the plurality of proximal and distal apices, wherein the coupling member is releasably secured to the delivery device,
where the coupling member comprises a ring portion that twists at least 30 degrees relative to the main body region to facilitate coupling of the stent to the delivery device,
where the ring portion is set into a circumferentially bent position relative to the main body region.

10. The system of claim 9, further comprising an extension segment positioned axially between the ring portion and the at least one of proximal and distal apices.

11. The system of claim 9, where an eyelet of the ring portion encircles a section of the delivery device in a delivery state.

12. The system of claim 9, where at least one of the ring portion and the extension segment comprise a wall thickness that is less than a wall thickness of other regions of the stent to facilitate twisting of the ring portion in a first direction relative to the main body region.

13. A system for deploying at least a portion of a stent, the system comprising:
a delivery device; and
a stent that is releasably secured to a portion of the delivery device,
where the stent comprises a main body region and proximal and distal ends,
where one of the proximal or distal ends of the stent comprises a plurality of apices that each comprises a coupling member that is releasably secured to the delivery device, where longitudinal positions of the coupling members of adjacent apices are axially staggered relative to each other,
where variable lengths of extension segments, which extend between the plurality of apices and respective coupling members, contribute to the axial staggering of the coupling members,
where each coupling member is twisted to facilitate coupling of the coupling member to the delivery device.

14. The system of claim 13, where each coupling member is set into a bent position to facilitate coupling of the coupling member to the delivery device.

15. The system of claim 13, where the delivery device comprises a cannula having an outer surface, and a coiled member having proximal and distal ends, where at least a portion of the coiled member is secured to the outer surface of the cannula,
where the coupling member is releasably secured to a portion of the coiled member.

16. The system of claim 15 where the coiled member has a plurality of turns disposed between the proximal and distal ends of the coiled member, and where the axial length differential between adjacent proximal apices is calculated based on a formula factoring into account at least the pitch of the coiled member.

17. The system of claim 15 where one of the proximal and distal ends of the coiled member is secured to the outer surface of the cannula, and the other of the proximal and distal ends of the coiled member is unsecured relative to the outer surface of the cannula,
where the coiled member has a plurality of turns disposed between the proximal and distal ends of the coiled member, and
where a portion of the stent is looped around the unsecured end of the coiled member and further is disposed within a spacing between adjacent turns of the coiled member.

18. A system for deploying at least a portion of a stent, the system comprising:
a delivery device; and
a stent that is releasably secured to a portion of the delivery device,
where the stent comprises a main body region and proximal and distal ends,
where one of the proximal or distal ends of the stent comprises a plurality of apices that each comprises a coupling member that is releasably secured to the delivery device, where longitudinal positions of the coupling members of adjacent apices are axially staggered relative to each other,
where the coupling members are configured to be loaded through a common engagement point of the delivery device.

19. A system for deploying at least a portion of a stent, the system comprising:
a delivery device; and
a stent that is releasably secured to a portion of the delivery device,
where the stent comprises a main body region and proximal and distal ends,
where one of the proximal or distal ends of the stent comprises a plurality of apices that each comprises a coupling member that is releasably secured to the delivery device, where longitudinal positions of the coupling members of adjacent apices are axially staggered relative to each other,
where the coupling members are set into a circumferentially bent position relative to the main body region.

* * * * *